(12) United States Patent
Wessel

(10) Patent No.: US 10,369,244 B2
(45) Date of Patent: Aug. 6, 2019

(54) INCENSE BURNER APPARATUS AND METHOD

(71) Applicant: TENNEN LLC, Phoenix, AZ (US)

(72) Inventor: Ethan Christopher Wessel, Phoenix, AZ (US)

(73) Assignee: TENNEN LLC, Phoenix, AZ (US)

( * ) Notice: Subject to any disclaimer, the term of this patent is extended or adjusted under 35 U.S.C. 154(b) by 164 days.

(21) Appl. No.: 15/280,326

(22) Filed: Sep. 29, 2016

(65) Prior Publication Data

US 2018/0085484 A1 Mar. 29, 2018

(51) Int. Cl.
*A61L 9/03* (2006.01)
*B23P 19/00* (2006.01)
*A61L 9/02* (2006.01)
*A61L 9/012* (2006.01)

(52) U.S. Cl.
CPC ............... *A61L 9/03* (2013.01); *B23P 19/00* (2013.01); *A61L 2209/15* (2013.01)

(58) Field of Classification Search
CPC ..... A61L 2209/15; A61L 19/03; A61L 19/037; A61L 19/012; B23P 19/00
USPC ........................................................ 431/325
See application file for complete search history.

(56) References Cited

U.S. PATENT DOCUMENTS

| | | | | |
|---|---|---|---|---|
| 1,530,103 A | * | 3/1925 | Booth | A61L 9/03 |
| | | | | 422/126 |
| 1,665,659 A | * | 4/1928 | Evans | A61L 9/03 |
| | | | | 131/238 |
| D242,639 S | * | 12/1976 | Patel | D27/125 |
| D245,992 S | * | 10/1977 | Gruber | D11/131.1 |
| D246,910 S | * | 1/1978 | Patel | D11/131.1 |
| D250,417 S | * | 11/1978 | Preston | D11/131.1 |

(Continued)

FOREIGN PATENT DOCUMENTS

| | | | |
|---|---|---|---|
| JP | 01297067 A | * | 11/1989 |
| JP | 08215028 A | * | 8/1996 |

(Continued)

OTHER PUBLICATIONS

Website, Naver blog; Feb. 17, 2015, retrieved from the Internet: <URL: http://blog.naver.com/happyhippy_/220276636076>; 17 pages; Korea.

(Continued)

*Primary Examiner* — Gregory L Huson
*Assistant Examiner* — Daniel E Namay
(74) *Attorney, Agent, or Firm* — Greenberg Traurig, LLP

(57) ABSTRACT

An incense holder assembly and method of manufacture. The incense holder assembly has a base including a cavity, and an ash collector, and an upper housing including a first end with an incense material support including an incense aperture that can support an incense structure inserted into the incense aperture. An external cavity is positioned coupled to the incense material support and the ash collector, and a channel fluidly extends from the incense aperture to an internal cavity. The assembly also includes incense material support surfaces that can support the incense structure by coupling to a side of the incense structure. An incense material support surface is positioned within a channel or the internal cavity, and an incense material support surface is adjacent to or proximate the at least one aperture.

21 Claims, 18 Drawing Sheets

(56) References Cited

U.S. PATENT DOCUMENTS

| | | | | |
|---|---|---|---|---|
| 4,275,746 | A | * | 6/1981 | Gruber ............... A24F 3/00 131/178 |
| D264,869 | S | * | 6/1982 | Gordon ............... D11/131.1 |
| 5,186,182 | A | | 2/1993 | Lin |
| 5,215,719 | A | * | 6/1993 | Newman ............ A61L 9/03 131/190 |
| 5,873,370 | A | * | 2/1999 | Towle ................ A24F 19/10 131/190 |
| 6,447,732 | B1 | * | 9/2002 | West ................. A61L 9/03 422/126 |
| 7,736,605 | B1 | * | 6/2010 | Gomez ............... A61L 9/03 362/161 |
| D804,985 | S | * | 12/2017 | Wessel ............... D11/131.1 |
| 2004/0241055 | A1 | * | 12/2004 | Padilla ............... A61L 9/03 422/126 |
| 2011/0214889 | A1 | * | 9/2011 | Sandberg ........... A62C 3/00 169/48 |
| 2014/0178055 | A1 | * | 6/2014 | Chen ................. A61L 9/03 392/390 |
| 2015/0297773 | A1 | * | 10/2015 | Mayberry ........... A61L 9/03 422/126 |

FOREIGN PATENT DOCUMENTS

| | | | | |
|---|---|---|---|---|
| JP | 11009429 | A | * | 1/1999 |
| JP | 2004313721 | A | * | 11/2004 |
| JP | 2005021549 | A | * | 1/2005 |
| JP | 2006-026132 | A | | 2/2006 |
| JP | 2006223778 | A | * | 8/2006 |
| JP | 2009219844 | A | * | 10/2009 |
| JP | 2017104457 | A | * | 6/2017 |
| WO | 2007/142633 | A1 | | 12/2007 |

OTHER PUBLICATIONS

Website, Naver blog Mar. 28, 2016, retrieved from the Internet: <URL: http://blog.naver.com/jsk9831/220667546575>; 7 pages; Korea.
Korean Intellectual Property Office; PCT International Search Report, Issued in Connection to PCT/US2017/053022; dated Feb. 8, 2018; 3 pages; Korea.
Korean Intellectual Property Office; PCT Written Opinion of the International Searching Authority, Issued in Connection to PCT/US2017/053022; dated Feb. 8, 2018; 8 pages; Korea.
European Patent Office; English Translation of Abstract of JP2006026132; dated Feb. 2, 2016; 1 page.

* cited by examiner

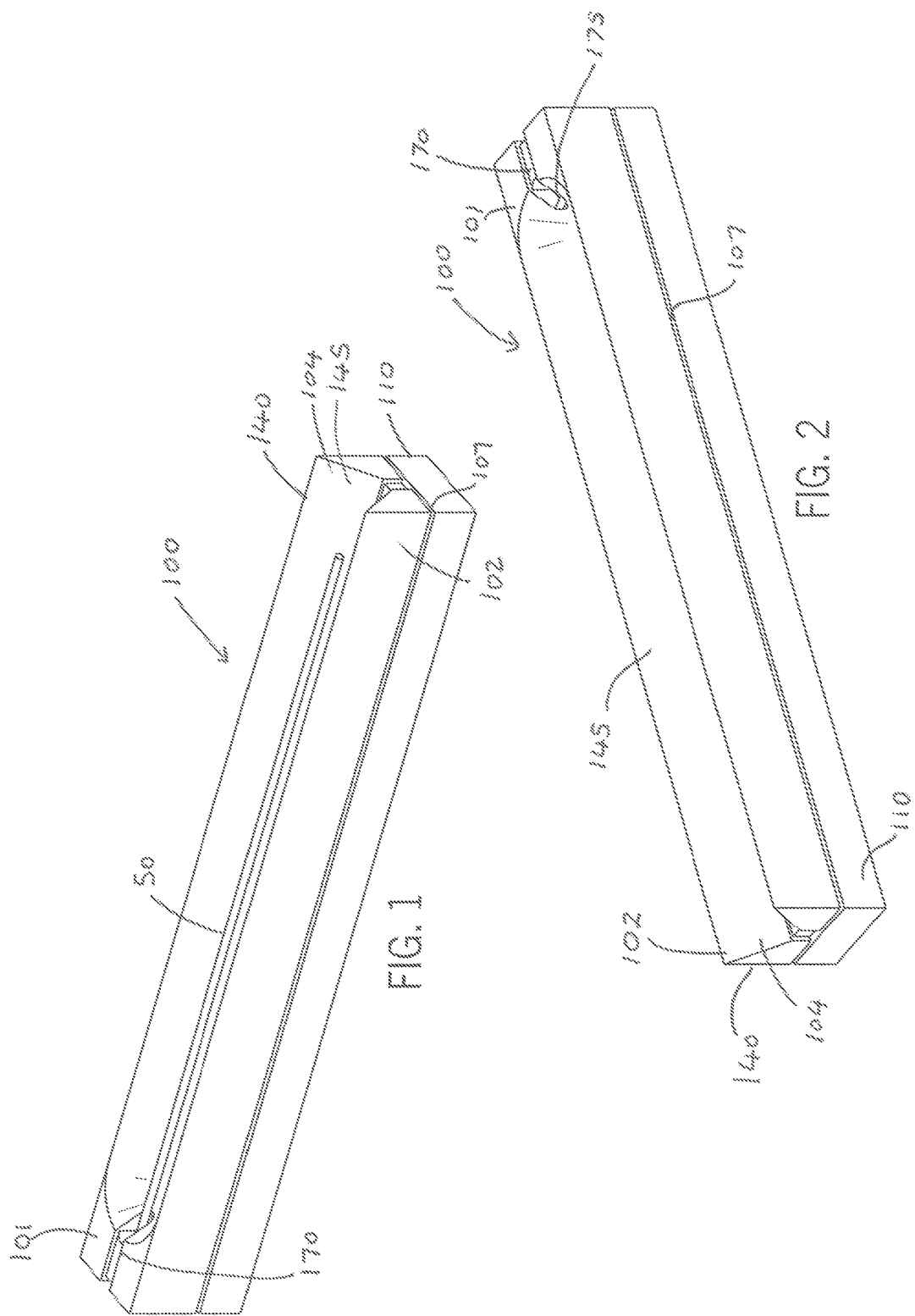

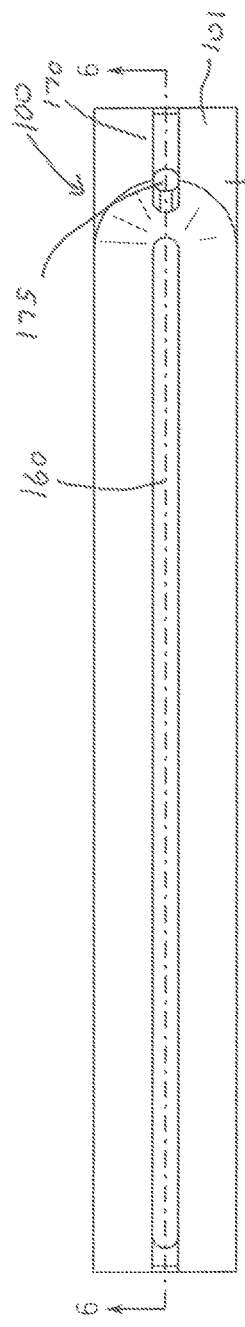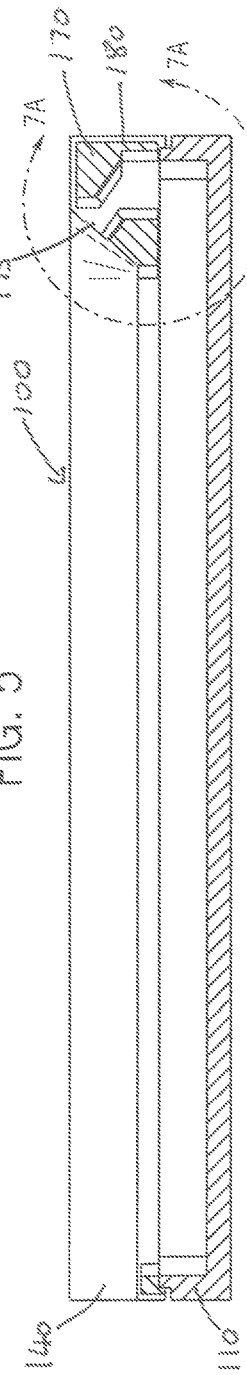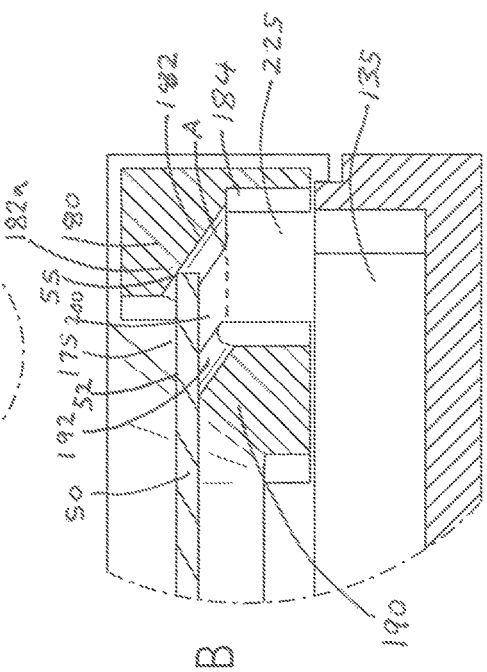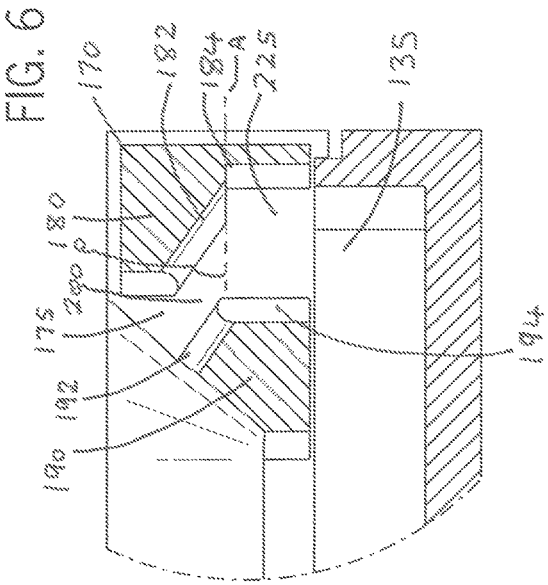
FIG. 5
FIG. 6
FIG. 7A
FIG. 7B

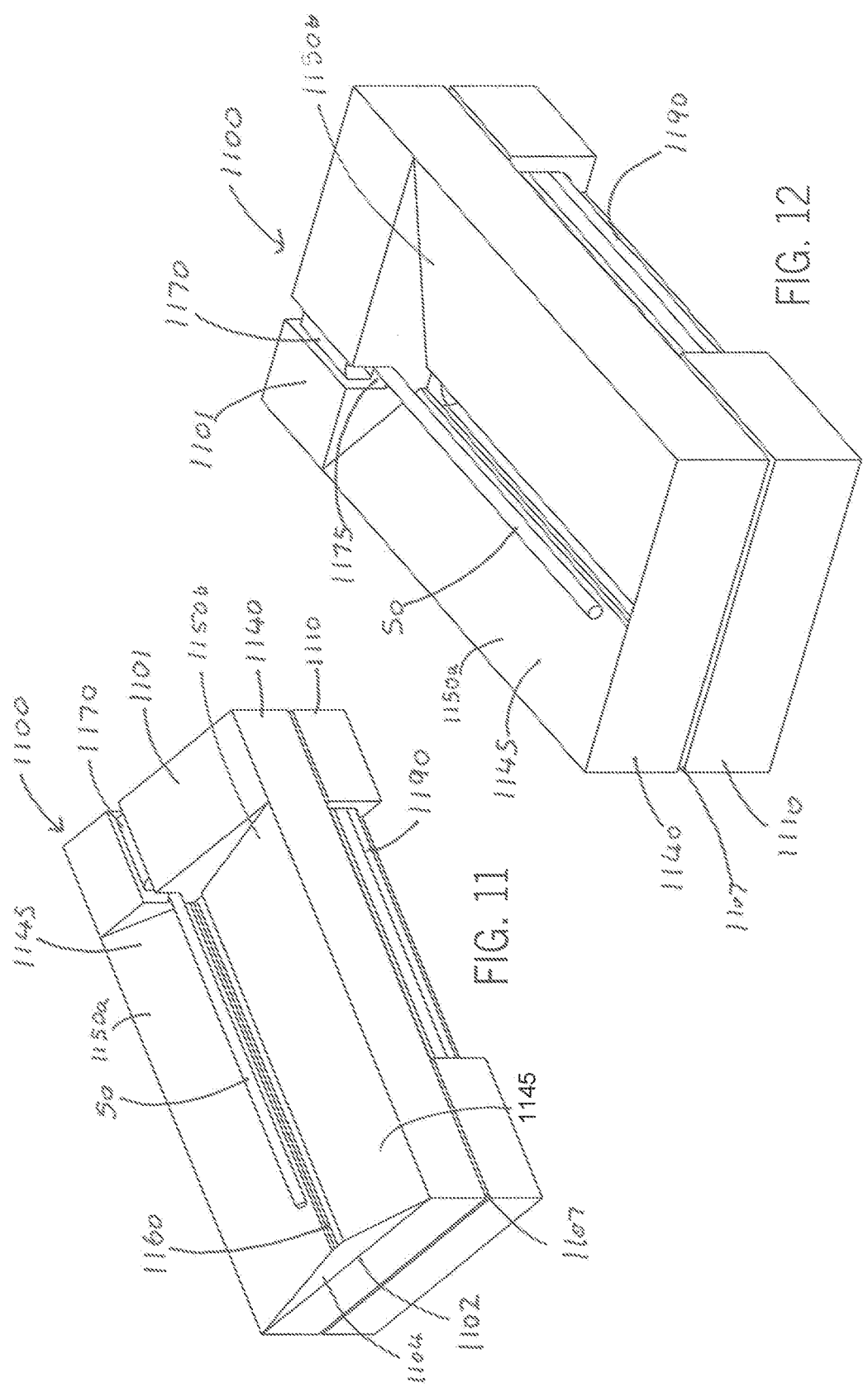

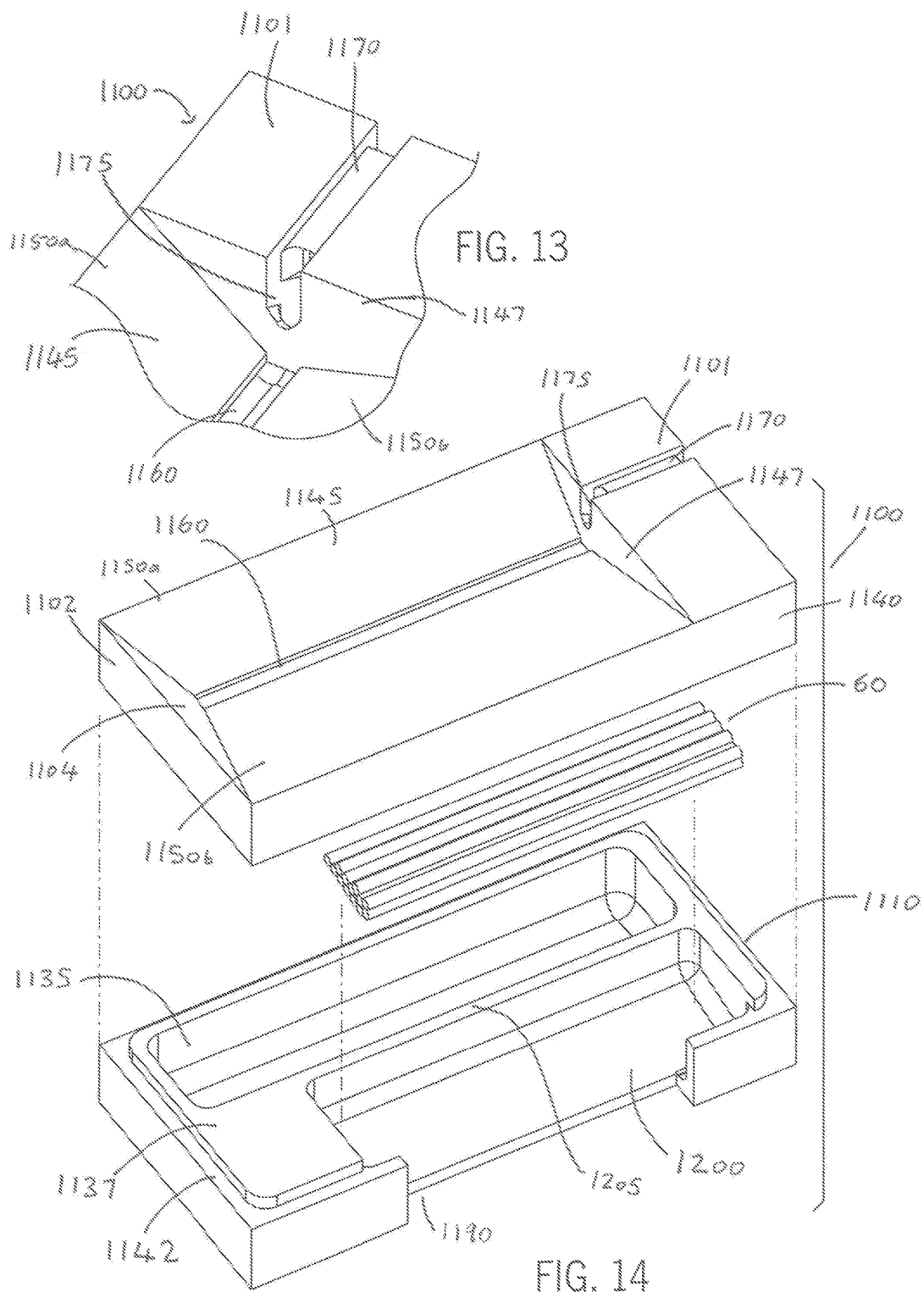

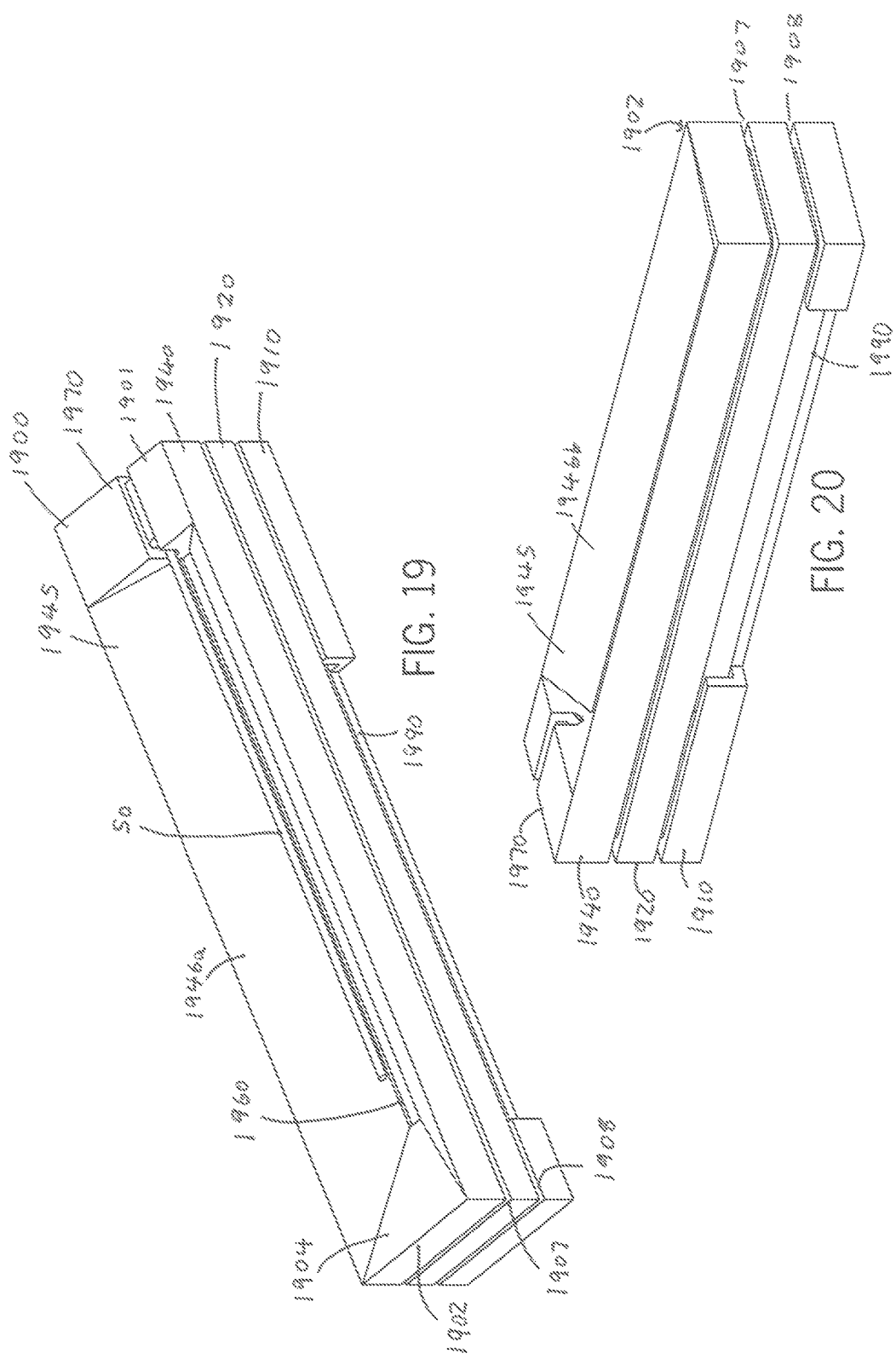

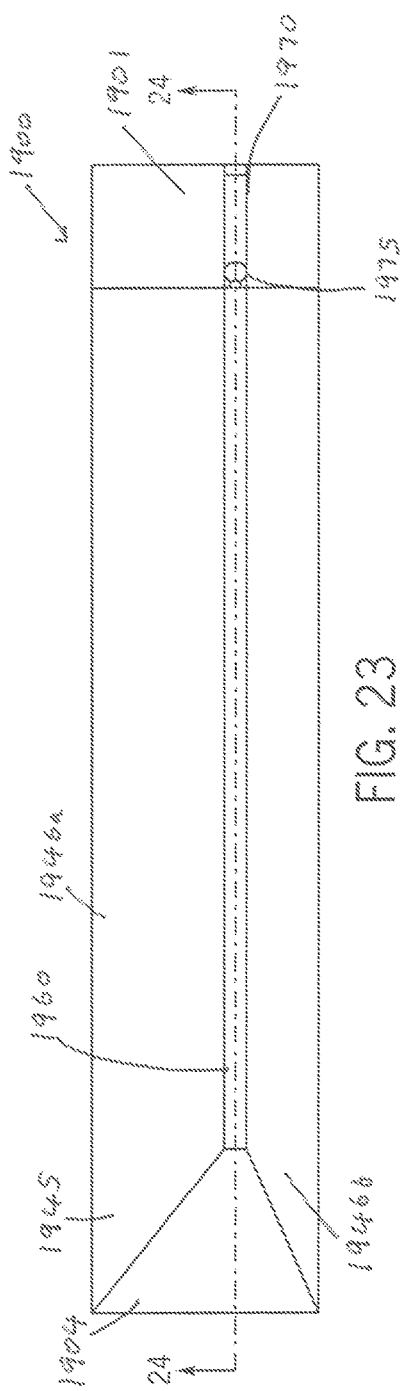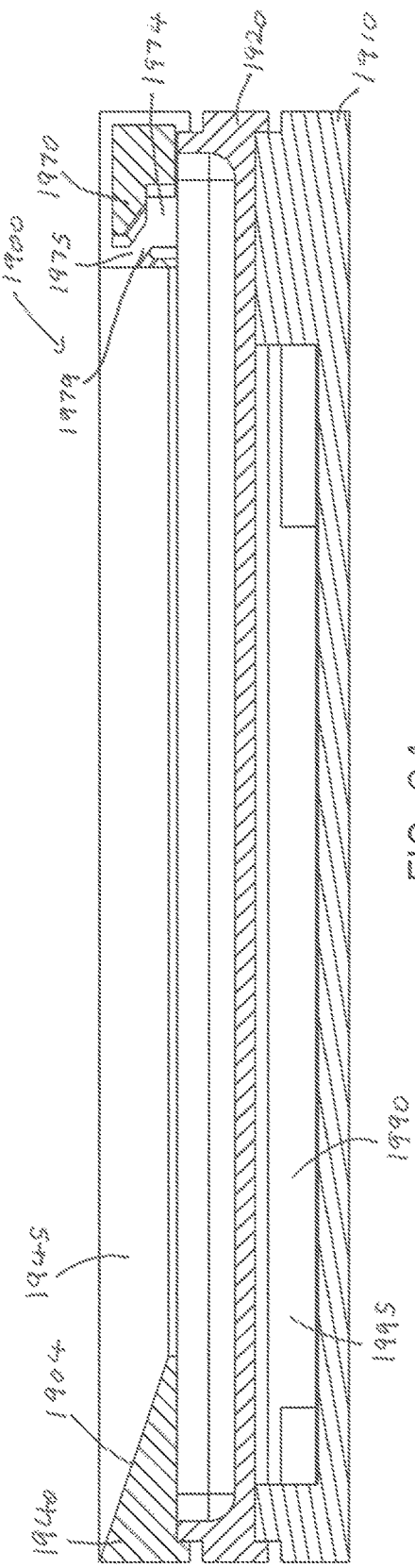

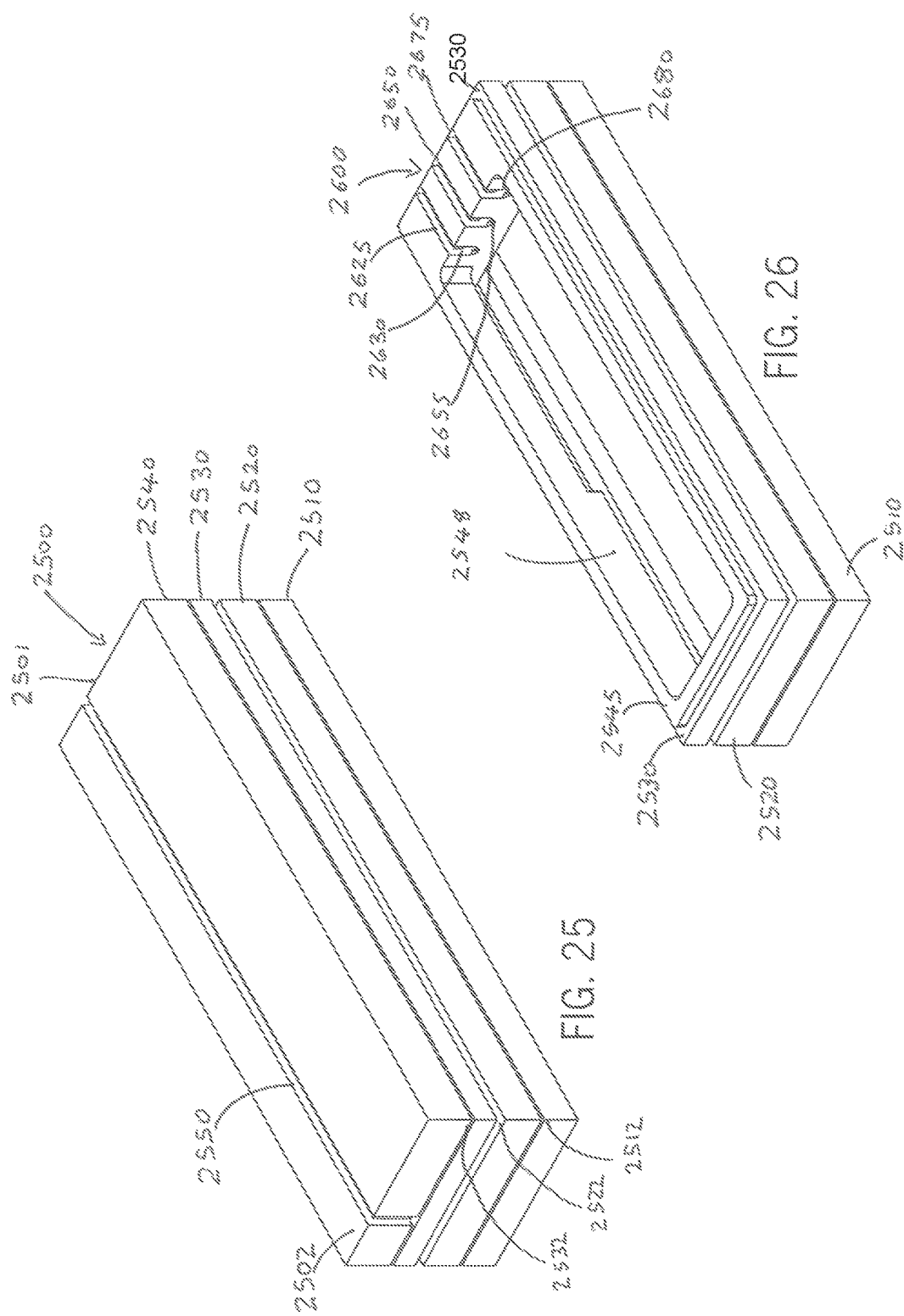

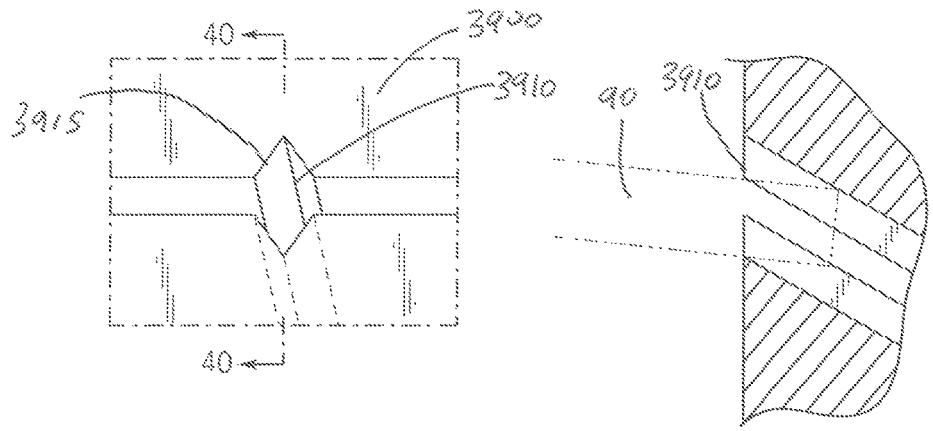
FIG. 39
FIG. 40
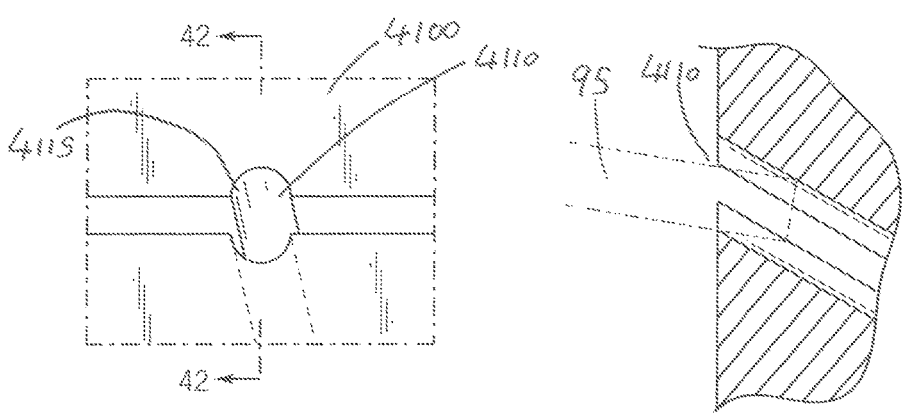
FIG. 41
FIG. 42
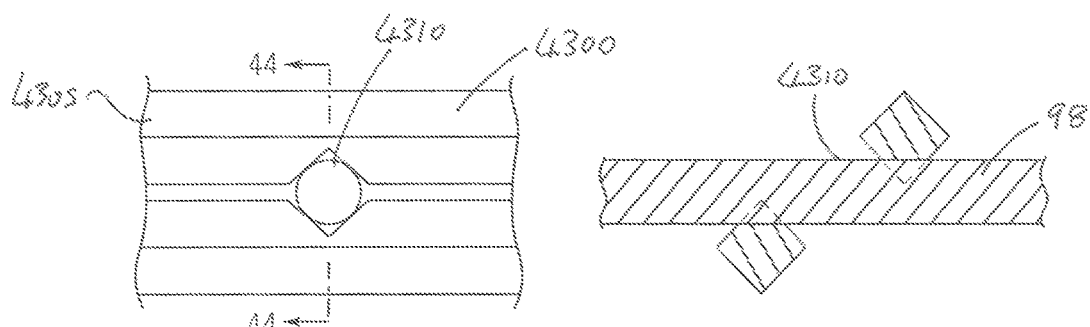
FIG. 43
FIG. 44

INCENSE BURNER APPARATUS AND METHOD

BACKGROUND

Incense has been used globally for many centuries, is especially popular in Asian countries, and has more recently gained popularity in the United States. Burning incense is used for aromatherapy and fragrance dispersal, as an insect repellent/insecticide, and for medicinal uses. Incense sticks or incense coils are the most popular physical shapes, and various types of dispensers and holders are available to store new incense materials prior to burning. Incense materials tend to be rapidly extinguished when positioned very close to or on a non-combustible surface. Incense materials therefore need to be supported so that most of any portion of the incense material that is intended to be burned is prevented from touching or coming close to another surface.

Burning incense typically creates ash and other debris that can be unsightly. Conventional incense burners generally do not enable efficient capture of ash and/or do not enable most of the incense product to be burned before replacement is necessary. The problem of ash and debris creation tends to influence potential incense consumers who are unwilling to consider manual collection and clean-up of incense waste. Accordingly, there exists a need for a device or apparatus that facilitates efficient burning of incense while also capturing some or all of the combustion byproducts and debris.

SUMMARY

Some embodiments include an incense holder assembly comprising at least one orifice coupled to at least one internal chamber of the incense holder assembly. The at least one orifice is configured and arranged with the at least one internal chamber as a cantilever support when coupled with at least one inserted incense material comprising a first predetermined length sufficient to maintain a certain cantilever load on at least a portion of the at least one orifice or at least one inner surface of the at least one internal chamber. Further, the certain cantilever load being a cantilever load sufficient to maintain the at least one inserted incense material in a stable position. Further, where following a reduction of the first predetermined length by burning to a second predetermining length that results in the at least one inserted incense material exerting an insufficient cantilever load on at least a portion of the at least one orifice and at least one inner surface of the at least one internal chamber, the at least one inserted incense material drops out of the at least on orifice and into the at least one internal chamber.

Some further embodiments of the invention include an incense holder assembly comprising at least one base including at least one cavity, and at least one ash collector coupled to the at least one base. The assembly can also include an upper housing comprising a first end including at least one incense material support which can include at least one incense aperture configured and arranged to support an incense structure inserted at least partially into the at least one incense aperture. The assembly may also include at least one external cavity positioned coupled to the at least one incense material support and coupled to the at least one ash collector. Further, the at least one channel be fluidly coupled from the at least one incense aperture to at least one internal cavity. The assembly also includes at least two incense material support surfaces configured and arranged to at least partially support the incense structure by coupling to at least one side of the incense structure. At least one of the at least two incense material support surfaces is positioned within at least one of the at least one channel and the at least one internal cavity. Further, at least one of the at least two incense material support surfaces is adjacent to or proximate the at least one aperture.

In some embodiments, the at least two incense material support surfaces are configured and arranged to provide support to the incense structure based at least in part on gravity-induced force on at least one of the at least two incense material support sides exerted by the incense structure.

In some embodiments, the upper housing includes the at least one external cavity. In some further embodiments, the at least one external cavity comprises at least two oppositely opposed sides extending from opposite sides of the at least one ash aperture. In some other embodiments, the at least one ash aperture is positioned substantially centrally in the upper housing extending from adjacent the at least one incense aperture at the first end at least partially to an opposite end of the upper housing.

In some embodiments, the at least one ash aperture is positioned off-center in the upper housing extending from adjacent the at least one incense aperture at the first end at least partially to an opposite end of the upper housing. In some embodiments, the at least one channel comprises the at least two incense material support surfaces. In some further embodiments, the at least one channel is configured and arranged to support an inserted incense stick extending at least partially from the first end of the upper housing towards an opposite end of the upper housing.

Some embodiments include at least one storage cavity. In some further embodiments, the at least one storage cavity is positioned in the at least one base layer and positioned at least partially beneath and separated from the at least one ash collector.

Some further embodiments of the invention include a lid coupled to the upper housing and extending at least partially across the at least one external cavity. In some embodiments, the lid includes at least one vent fluidly coupled to the at least one external cavity and the at least one incense aperture.

In some embodiments, the at least one incense material support comprises three incense material supports, where each incense material support includes an incense aperture. In some embodiments, the upper housing includes an open second end. In some further embodiments, the upper housing includes a closed second end, and the at least one external cavity comprises a trough. In some other embodiments, the at least one cavity comprises the at least one ash collector.

Some embodiments include an incense holder manufacturing method comprising forming at least one base including at least one cavity, and forming at least one ash collector in at least one ash collector layer. Some further embodiments include forming an upper housing comprising a first end including at least one incense material support configured to be coupled to the at least one base. The at least one incense material support includes at least one incense aperture configured and arranged to support an incense structure, and the upper housing includes at least one external cavity positioned coupled to the at least one incense material support. Further, the at least one external cavity is fluidly coupled to the at least one ash collector. Further, the method includes forming at least one channel fluidly extending from the at least one incense aperture to at least one internal cavity. Further, the method includes forming or assembling at least two incense material support surfaces configured and arranged to at least partially support the incense structure by coupling to at least one surface of the incense structure. At least one of the at least two incense material support surfaces is positioned within at least one of the at least one channel and the at least one internal cavity, and at least one of the at least two incense material support surfaces is adjacent to or proximate the at least one aperture.

In some embodiments, the at least two incense material support surfaces comprise at least one surface of at least one of the at least one base, the at least one ash collector and the upper housing. Some further embodiments of the method include forming at least one storage cavity positioned in the at least one base layer and positioned beneath and separated from the at least one ash collector. Other embodiments of the method include forming a lid configured to be coupled to the upper housing and extending at least partially across the at least one external cavity. The lid includes at least one vent fluidly coupled to the at least one external cavity and the at least one incense aperture.

Some embodiments include an incense holder manufacturing method comprising providing at least one base including at least one cavity, and providing at least one ash collector in at least one ash collector layer. Some further embodiments include providing an upper housing comprising a first end including at least one incense material support configured to be coupled to the at least one base. The at least one incense material support includes at least one incense aperture configured and arranged to support an incense structure, and the upper housing includes at least one external cavity positioned coupled to the at least one incense material support. Further, the at least one external cavity is fluidly coupled to the at least one ash collector. Further, the method includes providing at least one channel fluidly extending from the at least one incense aperture to at least one internal cavity. Further, the method includes providing or assembling at least two incense material support surfaces configured and arranged to at least partially support the incense structure by coupling to at least one surface of the incense structure. At least one of the at least two incense material support surfaces is positioned within at least one of the at least one channel and the at least one internal cavity, and at least one of the at least two incense material support surfaces is adjacent to or proximate the at least one aperture.

In some embodiments, the at least two incense material support surfaces comprise at least one surface of at least one of the at least one base, the at least one ash collector and the upper housing. Some further embodiments of the method include providing at least one storage cavity positioned in the at least one base layer and positioned beneath and separated from the at least one ash collector. Other embodiments of the method include providing a lid configured to be coupled to the upper housing and extending at least partially across the at least one external cavity. The lid includes at least one vent fluidly coupled to the at least one external cavity and the at least one incense aperture.

DESCRIPTION OF THE DRAWINGS

FIG. 1 is a perspective view of an incense burner in accordance with some embodiments of the invention.

FIG. 2 is a perspective view of an incense burner in accordance with some embodiments of the invention.

FIG. 5 is a top view of the incense burner of FIGS. 1-2 in accordance with some embodiments of the invention.

FIG. 6 is a cross-sectional view taken through the cross-section line shown in FIG. 5 in accordance with some embodiments of the invention.

FIG. 7A is a close-up view of a holder portion of the incense burner defined in the FIG. 6 in accordance with some embodiments of the invention.

FIG. 7B is a close-up of an end of the incense burner of FIG. 7A showing a partial portion of an incense stick positioned in the holder portion of the incense burner in accordance with some embodiments of the invention.

FIG. 11 is a top-front perspective view of an incense burner in accordance with some embodiments of the invention.

FIG. 12 is a perspective view of an incense burner in accordance with some embodiments of the invention.

FIG. 13 is a close-up cutaway perspective view of an end of the incense burner of FIGS. 11-12 in accordance with some embodiments of the invention.

FIG. 14 is an exploded assembly view of the incense burner of FIGS. 11-12 including incense sticks in accordance with some embodiments of the invention.

FIG. 19 is a top-front perspective view of an incense burner in accordance with some embodiments of the invention.

FIG. 20 is a perspective view of an incense burner in accordance with some embodiments of the invention.

FIG. 23 is a top view of the incense burner of FIGS. 19-20 in accordance with some embodiments of the invention.

FIG. 24 is a cross-sectional view taken through the cross-section line shown in FIG. 23 in accordance with some embodiments of the invention.

FIG. 25 is a perspective view of an incense burner in accordance with some embodiments of the invention.

FIG. 26 is a perspective view of the incense burner of FIG. 25 with the lid portion removed in accordance with some embodiments of the invention.

FIG. 39 is an elevation view of an incense stick orifice in accordance with some embodiments of the invention.

FIG. 40 is a section view of the incense stick orifice of FIG. 39 in accordance with some embodiments of the invention.

FIG. 41 is an elevation view of an incense stick orifice in accordance with some embodiments of the invention.

FIG. 42 is a section view of the incense stick orifice of FIG. 41 in accordance with some embodiments of the invention.

FIG. 43 is an elevation view of an incense stick orifice in accordance with some embodiments of the invention.

FIG. 44 is a section view of the incense stick orifice of FIG. 43 in accordance with some embodiments of the invention.

DETAILED DESCRIPTION

Figure 3:
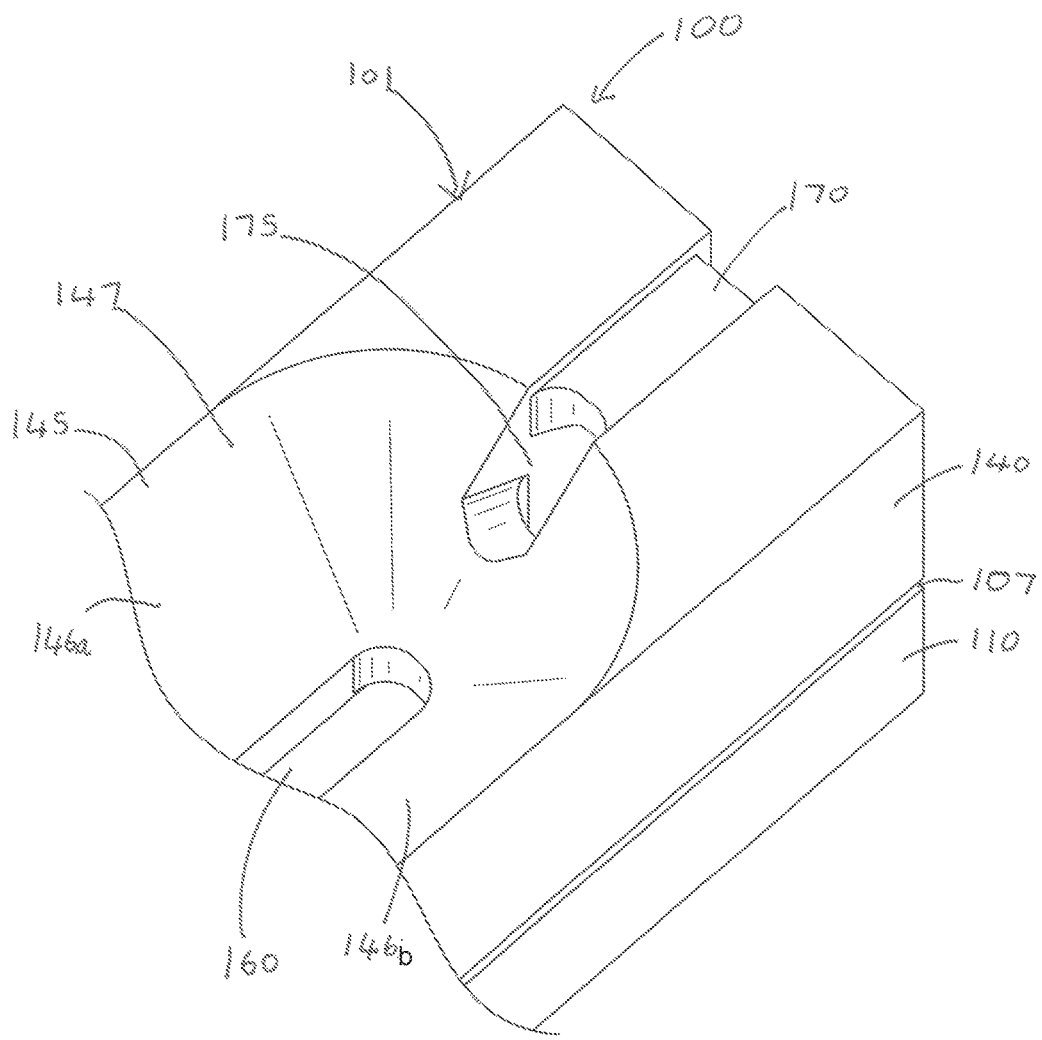
FIG. 3 is a close-up cutaway perspective view of an end of the incense burner of FIGS. 1-2 in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

The use of the term "burning" or variations thereof herein is meant to encompass a material, such as an incense material, wherein at least a portion of the incense material is initiating, undergoing, or completing combustion. Further, the term "combustion" or variations thereof herein is meant to encompass a material that is at least partially ignited, and is undergoing complete or incomplete combustion, is smoldering, is flaming, is smoking, or a combination thereof. While in use, the apparatus may be used to support a material that is at least partially burnt and/or includes a portion that is burning. In some embodiments, the apparatus can be used to support a material where at least a portion of the materials is undergoing combustion that is visible (i.e., includes a flame, and/or a glowing ember, smoke emission, ash formation, or a combination thereof). In other embodiments, the apparatus can be used to support a material where at least a portion of the material is undergoing combustion that is not visible (e.g., where any underlying combustion occurs in a bulk of the material and/or at least partially beneath a layer of ash or other combusted or partially burnt incense material.). In some further embodiments, any of the apparatus or assemblies described here can be used to hold or support one or more incense materials that are not lit or otherwise burning.

Unless specified or limited otherwise, the use of the term "incense" or variations thereof is meant to encompass a material, such as an incense material that can comprise a generally combustible base material, and can include a fragrance, perfume, incense oil, dry resin composition, or a combination thereof. The incense can comprise a wooden, paper, or other naturally derived cellulosic material coated in a composite of resin with incense powder and a filler such as sawdust and a resin. Other variations can include incense material comprising a cast-shaped, molded, or extruded composite of resin and/or glue with incense powder and a filler such as sawdust, or any other cellulosic-based material. Other additives can include an insect repellent (e.g., such as a mosquito repellent and/or pesticide), a medicine or health-enhancement material, smoke generator, or a combination thereof. In some embodiments, any incense material described herein and/or any commercial incense material can be burnt within one or more of the apparatus embodiments described herein.

One or more of the embodiments described herein can be configured to hold or mount one or more incense containing structures in stick or rod form (e.g., an incense stick or joss stick). As used herein, the terms incense stick and joss stick are used interchangeably. Further, one or more of the embodiments described herein can be configured to hold or mount one or more incense sticks that can be of any cross-sectional shape, including perfect or imperfect circles, perfect or imperfect triangles, perfect or imperfect rectangles, or portions with any combination of these cross-sectional shapes. In some further embodiments, one or more of the embodiments described herein can be configured to hold or mount one or more incense containing structures formed as pellets, tabs, blocks, cubes, or random chunks, or combinations thereof.

Some embodiments of the invention relate to an incense burner or assembly. In some embodiments, the incense burner or assembly can include a base including or coupled to an incense material support structure. Some embodiments include a waste collection portion or cavity. Some further embodiments include an incense material storage area or structure or cavity. Other embodiments can include additional support structures and/or cavities. For example, some embodiments include a plurality of storage cavities. Some further embodiments include one or more spacers to enable the size, height, and shape of the incense burner to be adjusted or changed by the manufacturer and/or user.

In general, while in use, the incense burner can be used with one or more incense materials where any portion or region of the incense material can be ignited by a user. In some embodiments, a user can mount a pre-lit incense stick, and in other embodiments, the user can mount an unlit incense stick which can then be subsequently lit by the user while mounted in the incense burner. In the case of a stick-shaped incense material, an igniter (e.g., such as a lighter or match) can be used to ignite one end of the stick while the other end is held, mounted, supported or coupled to the incense burner. For example, in some embodiments, one end of the incense stick can be inserted into the incense burner and held within an opening or aperture. The other end of the stick can be exposed and can project outwardly from the incense burner so that a portion of the stick extends into the air. Accordingly, some embodiments include an incense burner with a structure that can provide support for the incense material to enable at least a portion of incense material to be held in a free space, and not in contact with any portion of the incense burner or other structure or surface. Further, some embodiments include an incense burner with a structure that can provide support for the incense material to enable at least a portion of incense material to be held in a free space, and not less than about 1 mm from any portion of the incense burner or other structure or surface.

Referring initially to FIGS. 1 and 2, showing perspective views of an incense burner 100 in accordance with some embodiments of the invention, in some embodiments, the incense burner 100 can include a structure that provides an observer with a view of a supported incense material. Due to the open architecture of the incense burner 100 embodiment shown in FIGS. 1 and 2, a user can be enabled to view an incense material (e.g., such as the incense stick 50 shown in FIG. 1) in the incense burner during the combustion, and in some circumstances, can view any visible release of volatile combustion products and/or smoke. For example, in some embodiments, the incense burner 100 can hold the incense stick 50 in an upper portion 140, allowing combustion to proceed, while enabling volatile combustion products and/or smoke to be released into the air. In some embodiments, the incense burner 100 can include a base 110 on which at least a portion of the upper portion 140 is supported. In some embodiments, the incense burner 100 including the upper portion 140 at least partially coupled to the base 110. In some embodiments, the base 110 and upper portion 140 can be coupled substantially seamlessly where the transition from the base 110 to the upper portion 140 is barely visible or not visible to the user (not shown). In some embodiments, the base 110 and upper portion 140 can be coupled to provide a visible gap or seam 107.

Some embodiments comprise a first end 101 that includes an incense support 170, where a user can insert an incense stick 50 into the incense support 170 through an aperture 175. In some embodiments, the aperture 175 can be formed or positioned in any of the housings or portions of the incense burner 100 described herein. As mounted, the incense stick 50 can extend at least a partial length of the incense burner 100 towards the second end 102 of the incense burner 100. In some embodiments, the upper portion 140 can comprise a trough, cavity, or aperture extending at least a partial length of the upper portion 140. For example, in some embodiments, the upper portion 140 can comprise a cavity 145. In some embodiments, the cavity 145 can extend from the first end 101 extending away from the incense support 170 towards the second end 102. In some embodiments, the cavity 145 can comprise an open end 104 as shown in the non-limiting embodiment of FIGS. 1 and 2. In some embodiments, the incense stick 50 can extend beyond the second end 102 of the incense burner 100 by passing through the open end 104. In other embodiments, the cavity 145 can comprise a closed end (not shown).

Figure 4:
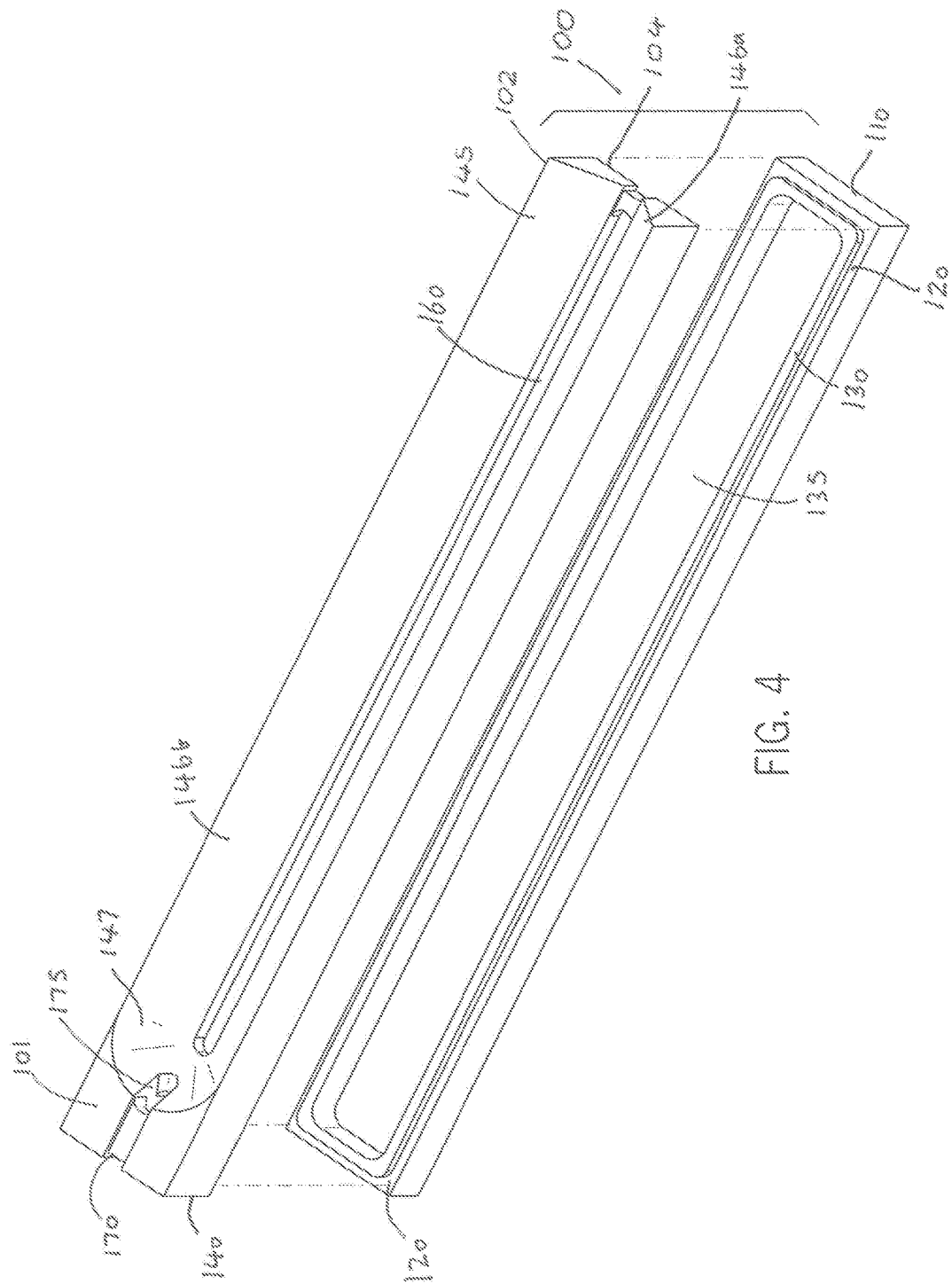
FIG. 4 is an exploded assembly view of the incense burner of FIGS. 1-2 in accordance with some embodiments of the invention.

FIG. 3 is a close-up cutaway perspective view of an end of the incense burner of FIGS. 1-2 in accordance with some embodiments of the invention, and FIG. 4 is an exploded assembly view of the incense burner of FIGS. 1-2 in accordance with some embodiments of the invention. In some embodiments, the cavity 145 can comprise two oppositely opposed coupled sides 146a, 146b inwardly extending to opposite edges of an ash aperture 160. In some embodiments, the ash aperture 160 is positioned substantially centrally in the upper portion 140 and the sides 146a 146b can be substantially the same width. In other embodiments, the ash aperture 160 can be positioned substantially centrally in the upper portion 140 and the sides 146a 146b can be of unequal width. As shown in FIG. 3, in some embodiments, the sides 146a, 146b can extend to a curved region 147 at the first end 101. Further, in some embodiments, the curved region 147 can extend from the sides 146a, 146b at the first end 101 adjacent the incense support 170 where the aperture 175 of the incense support 170 is positioned though a portion of the curved region 147.

In some embodiments, the incense burner 100 can include or comprise an ash collection region. In some other embodiments, a separate ash collection portion can be mounted to a separate base structure. During use, while any portion of an incense stick 50 is undergoing combustion, any ash product or other debris formed during combustion can fall under gravity from the incense stick 50 and travel into the ash collection region. In some embodiments, any ash arriving in the ash collection region can be out of sight of a user. In some embodiments, the ash collection region can be configured to be readily separable from other portions of the incense burner 100 to enable emptying and disposal of any collected ash product. For example, in some embodiments, the ash aperture 160 can be positioned so that products of combustion (e.g., such as ash or embers from the incense stick 50) can be received, collected, and/or stored for later disposal. For example, in some embodiments, material from the incense stick 50 can fall through any portion of the ash aperture 160 into the base 110. Referring to FIG. 4, in some embodiments, the base 110 can include an inner perimeter wall 130 extending around the perimeter of an ash tray 135 of the base 110. Further, the upper portion 140 can be positioned on the base 110 proximate to or coupled to a ledge 120 extending around the outer perimeter of the base 110 proximate the inner perimeter wall 130. When positioned as described (and shown in FIGS. 1 and 2), the base 110 of the incense burner 100 can function as a collection region for ash or other combustion products, where burnt or unburnt portions of the incense stick 50 travel through the ash aperture 160 and into the ash tray 135.

The architecture of the incense burner 100 can enable an incense stick 50 to burn efficiently by suspending the burning end or portion of the incense stick 50 in open space while allowing optimal capture of ash and other solid waste products from the incense stick 50. Further, in some embodiments, one or more internal surfaces or structures of the incense support 170 can enable the incense stick 50 to be positioned mostly or completely within the cavity 145 so that any burning portion of the incense stick 50 is containing generally within the cavity 145, and does not extend out of the incense burner 100 which may cause a safety hazard. The internal structures responsible for maintaining the position of the incense stick 50 are detailed in FIGS. 5-6, and 7A-7B and described in more detail in the following paragraphs.

FIG. 5 is a top view of the incense burner 100 of FIGS. 1-2 in accordance with some embodiments of the invention, and FIG. 6 is a cross-sectional view taken through the cross-section line shown in FIG. 5 in accordance with some embodiments of the invention. Further, FIG. 7A is a close-up view of a holder portion of the incense burner defined in the FIG. 6 in accordance with some embodiments of the invention, and FIG. 7B is a close-up of an end of the incense burner of FIG. 7A showing a partial portion of an incense stick 50 positioned in the holder portion of the incense burner in accordance with some embodiments of the invention. As discussed earlier, the incense stick 50 can be inserted into the incense support 170 through an aperture 175. Based at least on part on the internal structure of the aperture 175 and/or the shape of the inserted incense stick 50, the incense stick 50 can be positioned at various angles with respect to the incense burner 100. For example, in some embodiments, the aperture 175 can be formed through the first end 101 of the incense burner 100 and bounded by an upper portion 180 and a lower portion 190 that includes walls that at least partially bound the aperture 175, and a coupled channel 225 that is coupled to the ash tray 135. In some embodiments, the aperture 175 can form an entry to at least one cavity 145 that is created by a combination of walls or surfaces of the upper portion 180 and lower portion 190. In some embodiments, the aperture 175 can comprise a generally round cross-sectional profile. In other embodiments, the cross-sectional profile can be oval or ellipsoidal. In other embodiments, at least a portion of the cross-sectional profile of the aperture 175 can include a square or rectangular profile. Other embodiments include an aperture 175 with straight and round edge sections.

In some embodiments, the aperture 175 can form a portion of and/or entry to a channel 200 that can extend from the aperture 175 towards the coupled channel 225 to an interface (marked as dotted line plane A). Further, the channel 200 can be fluidly coupled to a section or region of the incense burner for collecting ash and other debris (e.g., the ash tray 135). In some embodiments, the aperture 175 can be bounded by an upper wall 182 extending from the aperture 175 at a region 147 of the cavity 145 to a coupled channel 225. In some embodiments, the coupled channel 225 can be formed between wall 184 extending from the upper portion 180 towards the ash tray 135, and wall 194 of the lower portion 190 that extends from the lower wall 192 to the ash tray 135.

In some embodiments of the invention, the channel 200 (formed and/or bounded by walls 182, 192) can be sloped or angled from the coupled channel 225. For example, in some embodiments, the angle P, taken from plane A can be about 30°. In some other embodiments, the angle P, taken from plane A can be more or less than about 30°. For example, in some embodiments, the angle P can be between about 0 and 15°. In some other embodiments, the angle A can be between about 15° and 30°. In some further embodiments, the angle P can be greater than about 30°. For example, in some embodiments, the angle P can be between about 30° and about 45°. In some other embodiments, the angle P can be between about 45° and about 60°. In some further embodiments of the invention, the angle P can be between about 60° and 80°. In further embodiments, the angle P can be greater than about 80° but less than about 90°.

Referring to FIG. 7B, in some embodiments, a first end 55 of the incense stick 50 can be inserted through the aperture 175. In some embodiments, a user can slide the incense stick 50 into the channel 200 until at least a portion of the first end 55 couples with upper wall 182 at a contact region 182a. In light of the above-mentioned angle P and variations of angle P with respect to plane A, one of ordinary skill in the art can recognize that the contact region 182a can change position based on a number of variables including, but not limited to the angle P, the extent to which the incense stick 50 is inserted into the channel 200, the geometry of the first end 55 of the incense stick 50, or a combination thereof.

In some embodiments, the incense stick 50 can remain in a generally stable position following insertion into the channel 200. Due to gravity, the mass of the incense stick 50 can exert a force against the upper wall 182 in the contact region 182a and the lower wall 192 at the interface with the region 147. Moreover, friction between the outer surface of the incense stick 50 (either at the end 55 or another portion of the outer surface of the incense stick 50 such as a region 52 adjacent to the end 55) and the contact region 182a of the upper wall 182 and/or friction contact between the outer surface of the incense stick 50 and the lower wall 192 at the interface with the region 147 can maintain the incense stick 50 in a generally stable position. In some further embodiments, the incense stick 50 can remain in a generally stable position following insertion into the channel 200 where a user has partially inserted the incense stick 50. In this instance, friction between the outer surface of the incense stick 50 in a region 52 coupled to the lower wall 192 at the interface with the region 147 can maintain the incense stick 50 in a generally stable position.

In some embodiments, the position or stability of the position of the incense stick 50 can vary based on the length and/or mass of the incense stick 50. In some embodiments, once a previously inserted incense stick 50 is reduced in length and/or mass (e.g., due to burning), the incense stick 50 can begin to shift within the aperture 175 and channel 200. For instance, where a combination of friction between the outer surface of the incense stick 50 and a surface of the lower wall 192, and friction contact between the outer surface of the incense stick 50 and friction contact between the first end 55 and the contact region 182a maintains the incense stick 50 in a stable position, the position of the incense stick 50 can become unstable as the length and mass of the incense stick 50 is reduced due to reduction of mass following burning. For example, in some embodiments, due to gravity, the lower mass of the incense stick 50 can exert a reduced force against the upper wall 182 at the end 55, and/or any surface of the lower wall 192 (e.g., at the interface with the region 147) resulting in movement of the incense stick 50. In some embodiments, depending on the diameter or resulting burnt length and/or composition of the incense stick 50, the outer surface of the incense stick 50 can also decouple with the contact region 182a of the upper wall 182. In some further embodiments, the position of the incense stick 50 can become unstable following insertion into the channel 200 where a user has partially inserted the incense stick 50 so the friction between the outer surface of the incense stick 50 (e.g., region 52) and the surface of the lower wall 192 and/or friction contact between the outer surface of the incense stick 50 and the end 55 at the upper wall 182 ordinarily maintains the incense stick 50 in a stable position when the incense stick 50 is longer and/or has greater mass. In this instance, as the incense stick 50 burns and its length and mass decrease, friction between a portion of the incense stick 50 and the surface of the lower wall 192 at the interface with the region 147 and/or friction contact between the incense stick 50 at the end 55 and the upper wall 182 may lessen or no longer be present, thereby causing instability and/or movement of the incense stick 50. In some embodiments, the length and mass of the incense stick 50 can be reduced (due to burning) to a point where the stability of the position of the remaining portion of the incense stick 50 is no longer stable. In this instance, the remaining portion of the incense stick 50 can decouple from the upper wall 182, and slide and/or otherwise move over the surface of the lower wall 192, and travel into the channel 200.

Figure 8:
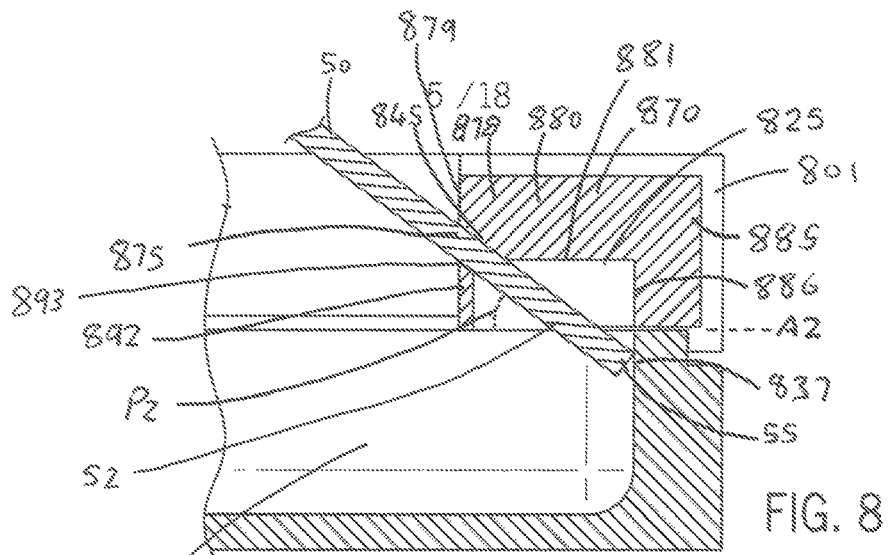
FIG. 8 shows a cross-sectional view of a holder portion in accordance with some further embodiments of the invention.

In some embodiment, one or more portions of the incense support 170, aperture 175, channel 200, and/or coupled channel 225 can vary while providing similar or substantially, identical function. For example, in some embodiments, FIG. 8 shows a cross-sectional view of an incense support 870 in accordance with some further embodiments of the invention. The incense support 870 is shown with a partial portion of an incense stick 50 positioned in the incense support 870. In some embodiments, the incense stick 50 can be inserted into the incense support 870 through an aperture 875 formed in the incense support 870 between one or more internal walls or surfaces of the incense support 870. In some embodiments, the aperture 875 can comprise a generally round cross-sectional profile. In other embodiments, the cross-sectional profile can be oval or ellipsoidal. In other embodiments, at least a portion of the cross-sectional profile of the aperture 875 can include a square or rectangular profile. Other embodiments include an aperture 875 with straight and round edge sections, Based at least in part on this internal structure of the incense support 870 including the aperture 875, the incense stick 50 can be positioned at various angles with respect to incense support 870 as part of an incense burner (e.g., such as incense burner 100).

In some embodiments, the aperture 875 can be formed by at least a portion of an upper section 880 and a lower section 892 that includes walls and surfaces that at least partially bound the aperture 875 and an internal cavity 825 that is fluidly coupled to ash tray 835. In some embodiments, the aperture 875 can form an entry to internal cavity 825 created by a combination of these walls or surfaces of the upper section 880 and lower section 892. For example, in some embodiments, the incense support 870 can comprise an upper section 880 inwardly extending from the first end 801 coupled to an end section 885 at the first end 801. In some embodiments, the end section 885 can be positioned extending generally perpendicular from the upper section 880, and generally parallel to the lower section 892. In some embodiments, the upper section 880 and end section 885 can at least partially surround the internal cavity 825. Further, in some embodiments, the internal cavity 825 can comprise a top side 881 of the upper section 880, and an end side 886 of the end section 885 that can extend generally perpendicular from the top side 881. In some embodiments, the lower section 892 can form another side of the internal cavity opposite the end side 886. In some embodiments, at a second end 878 of the upper section 880, an end wall 879 can extend towards the internal cavity 825 generally perpendicular to the end side 886. In some embodiments, the end wall 879 can couple with an aperture wall 845. The aperture wall 845 can extend inwardly towards the internal cavity 825 and couple with the top side 881 with a separation from an aperture wall 893 of the lower section 892 that forms the aperture 875.

As shown in the non-limiting embodiment of FIG. 8, an incense stick 50 can be positioned through the aperture 875 supported by the aperture walls 845, 893. In some embodiments, the incense stick 50 can be positioned as shown with a region 52 of the incense stick 50 generally positioned in the internal cavity 825, and the end 55 extending into the ash tray 835 and coupling with the cavity wall 837. In other embodiments, the incense stick 50 can be positioned through the aperture 875 supported by the aperture walls 845, 893, with a region 52 generally positioned in the internal cavity 825, and the end 55 extending into the ash tray 835 and/or the internal cavity 825 while not coupling with either the end side 886 and/or the cavity wall 837. As shown, when the incense stick 50 includes an outer diameter that is substantially the same or similar as the distance between any portion of the aperture walls 845 893, the incense stick 50 can be positioned angled at an angle P2 from plane A2 (comprising the interface between the internal cavity 825 and the ash tray 835), where the angle P2 is substantially the same as the angle of the aperture wall 845 from the top side 881. One of ordinary skill in the art can appreciate that the angle P2 can vary based on numerous factors, including, but not limited to, the diameter and/or shape of the incense stick 50, the extent to which the incense stick 50 extends into the internal cavity 825, the diameter of the aperture 875, and the angle of the aperture wall 845 with respect to the plane A2. For example, in some embodiments, the length of the end wall 879 and/or the length of the top side 881 can vary which can cause the angle of the aperture wall 845 with respect to the plane A2 to change (with the embodiment shown being substantially the same as the angle P2 as described earlier). In some embodiments, the angle of the aperture wall 845 with respect to the plane A2 can be about 45° as shown. In some embodiments, the angle of the aperture wall 845 with respect to the plane A2 can be more or less than about 45°. For example, in some embodiments, the angle of the aperture wall 845 with respect to the plane A2 can be less than 45° as shown. In some other embodiments, the angle of the aperture wall 845 with respect to the plane A2 can be greater than 45°.

In some embodiments, the incense stick 50 can remain in a generally stable position following insertion into the aperture 875. Due to gravity, the mass of the incense stick 50 can exert a force against the aperture walls 845, 893. Moreover, friction between the outer surface of the incense stick 50 (either at the end 55 or another portion of the outer surface of the incense stick 50 such as a region coupled to the aperture walls 845, 893) can maintain the incense stick 50 in a generally stable position. In some embodiments, the position or stability of the position of the incense stick 50 can vary based on the length and/or mass of the incense stick 50. In some embodiments, once a previously inserted incense stick 50 is reduced in length and/or mass (e.g., due to burning), the incense stick 50 can begin to move within the aperture 875 and/or internal cavity 825, and/or cavity wall 837. For instance, in some embodiments, where friction between the outer surface of the incense stick 50 and walls 879, 937, and/or friction between the outer surface of the incense stick 50 and the aperture 875 (e.g., between the incense stick 50 and either or both of the aperture walls 845, 893) can maintain the incense stick 50 in a stable position, the position of the incense stick 50 can become unstable as the length and mass of the incense stick 50 is reduced during burning, example, in some embodiments, due to gravity, the lower mass of the incense stick 50 can exert a reduced force against any of the walls 879, 937, 845, 893 which can result in movement of the incense stick 50. In some further embodiments, depending on the diameter or resulting burnt length and/or composition of the incense stick 50, the outer surface of the incense stick 50 can also decouple with any of the walls 879, 937, 845, 893. In some embodiments, the length and mass of the incense stick 50 can be reduced to a point where the stability of the position of the remaining portion of the incense stick 50 is no longer stable, the incense stick 50 can decouple from any of the walls 879, 937, 845, 893, and fall into the internal cavity 825 and the ash tray 835.

Figure 9:
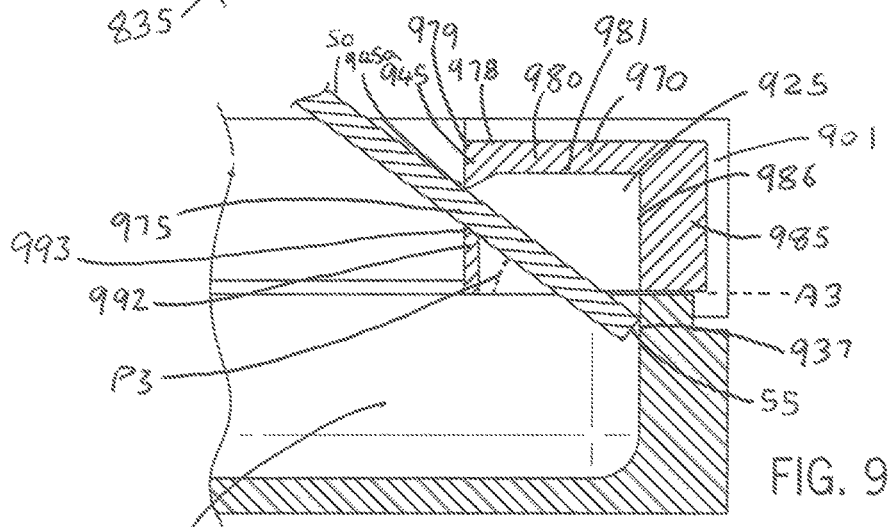
FIG. 9 shows a cross-sectional view of a holder portion in accordance with another embodiment of the invention.

FIG. 9 shows a cross-sectional view of an incense support 970 in accordance with some further embodiments of the invention. The incense support 970 is shown with a partial portion of an incense stick 50 positioned in the incense support 970. In some embodiments, the incense stick 50 can be inserted into the incense support 970 through an aperture 975 formed in the incense support 970 between one or more internal walls or surfaces of the incense support 970. In some embodiments, the aperture 975 can comprise a generally round cross-sectional profile. In other embodiments, the cross-sectional profile can be oval or ellipsoidal. In other embodiments, at least a portion of the cross-sectional profile of the aperture 975 can include a square or rectangular profile. Other embodiments include an aperture 975 with straight and round edge sections. Based at least on part on this internal structure of the incense support 970 including the aperture 975, the incense stick 50 can be positioned at various angles with respect to incense support 970 as part of an incense burner (e.g., such as incense burner 100). In some embodiments, the aperture 975 can be formed by at least a portion of an upper section 980 and a lower section 992 that includes walls and surfaces that at least partially bound the aperture 975 and an internal cavity 925 that is fluidly, coupled to ash tray 935. In some embodiments, the aperture 975 can form an entry to internal cavity 925 created by a combination of these walls or surfaces of the upper section 980 and lower section 992. For example, in some embodiments, the incense support 970 can comprise an upper section 980 inwardly extending from the first end 901 coupled to an end section 985 at the first end 901. Further, in some embodiments, the end section 985 can be positioned extending generally perpendicular from the upper section 980, and generally parallel to the lower section 992. In some embodiments, the upper section 980 and end section 985 at least partially surround the internal cavity 925. In some embodiments, the internal cavity 925 can comprise a top side 981 of the upper section 980, and an end side 986 of the end section 985 that extends generally perpendicular from the top side 981. In some embodiments, the lower section 992 can form another side of the internal cavity opposite the end side 986. In some further embodiments, at a second end 978 of the upper section 980, an end wall 979 can extend towards the internal cavity 925 generally perpendicular to the end side 986. In some embodiments, the end wall 979 can couple with an extension 945. In some embodiments, the extension 945 can extend towards the lower section 992 and couple with the top side 981 with a separation from an aperture wall 993 of the lower section 992 that forms the aperture 975. In the non-limiting embodiment of FIG. 9, the extension is shown extending away from the upper section 980 to form a blunt or pointed end 945a. In some embodiments, the blunt or pointed end 945a can comprise a generally rounded and/or flat surface.

As shown in the non-limiting embodiment of FIG. 9, an incense stick 50 can be positioned through the aperture 975 supported by the aperture wall 993 and blunt or pointed end 945a. In some embodiments, the incense stick 50 can be positioned as shown with a region 52 generally positioned in the internal cavity 925, and the end 55 of the incense stick 50 extending into the ash tray 935 and coupling with the cavity wall 937. In other embodiments, the incense stick 50 can be positioned through the aperture 975 supported by the aperture wall 993 and blunt or pointed end 945a, with a region 52 generally positioned in the internal cavity 925, and the end 55 extending into the ash tray 935 and/or the internal cavity 925 while not coupling with either the end side 986 and/or the cavity wall 937. As shown, when the incense stick 50 includes an outer diameter that is substantially the same or similar as the distance between any portion of the aperture wall 993 and blunt or pointed end 945a, the incense stick 50 can be positioned angled at an angle P3 from plane A3 (comprising the interface between the internal cavity 925 and the ash tray 935), where the angle P3 is substantially the same as the angle of the extension 945 from the top side 981. One of ordinary skill in the art can appreciate that the angle P3 can vary based on numerous factors, including, but not limited to, the shape or diameter of the incense stick 50, the extent to which the incense stick 50 extends into the internal cavity 925, the diameter of the aperture 975, the extension 945 and/or blunt or pointed end 945a geometry, and the shape or angle of the aperture wall 993 with respect to the plane A3 (similar to that discussed above with respect to the variation of the aperture wall 845 with respect to the plane A2).

In some embodiments, the incense stick 50 can remain in a generally stable position following insertion into the aperture 975. Due to gravity, the mass of the incense stick 50 can exert a force against the aperture wall 993 and blunt or pointed end 945a of the extension 945. Moreover, friction between the outer surface of the incense stick 50 (either at the end 55 or another portion of the outer surface of the incense stick 50 such as a region coupled to the aperture wall 993 and blunt or pointed end 945a) can maintain the incense stick 50 in a generally stable position. In some embodiments, the position or stability of the position of the incense stick 50 can vary based on the length and/or mass of the incense stick 50. In some embodiments, once a previously inserted incense stick 50 is reduced in length and/or mass (e.g., due to burning), the incense stick 50 can begin to move within the aperture 975 and/or internal cavity 925, and/or cavity wall 937. For instance, where friction between the outer surface of the incense stick 50 and walls 993, 937, and/or friction between the outer surface of the incense stick 50 and the aperture 975 (e.g., between the incense stick 50 and either or both of the aperture wall 993 and blunt or pointed end 945a) can maintain the incense stick 50 in a stable position, the position of the incense stick 50 can begin to become unstable as the length and mass of the incense stick 50 is reduced during burning. In some embodiments, the lower mass of the incense stick 50 can exert a reduced force against any of the walls 979, 937, 993, and blunt or pointed end 945a which can result in movement of the incense stick 50. In some further embodiments, depending on the diameter or resulting burnt length and/or composition of the incense stick 50, the outer surface of the incense stick 50 can also decouple with any of the walls 979, 937, 993 and blunt or pointed end 945a. In some embodiments, the length and mass of the incense stick 50 can be reduced (due to burning) to a point where the stability of the position of the remaining portion of the incense stick 50 is no longer stable, the incense stick 50 can decouple from any of the walls 979, 937, 993, and blunt or pointed end 945a, and fall into the internal cavity 925 and the ash tray 935.

Figure 10:
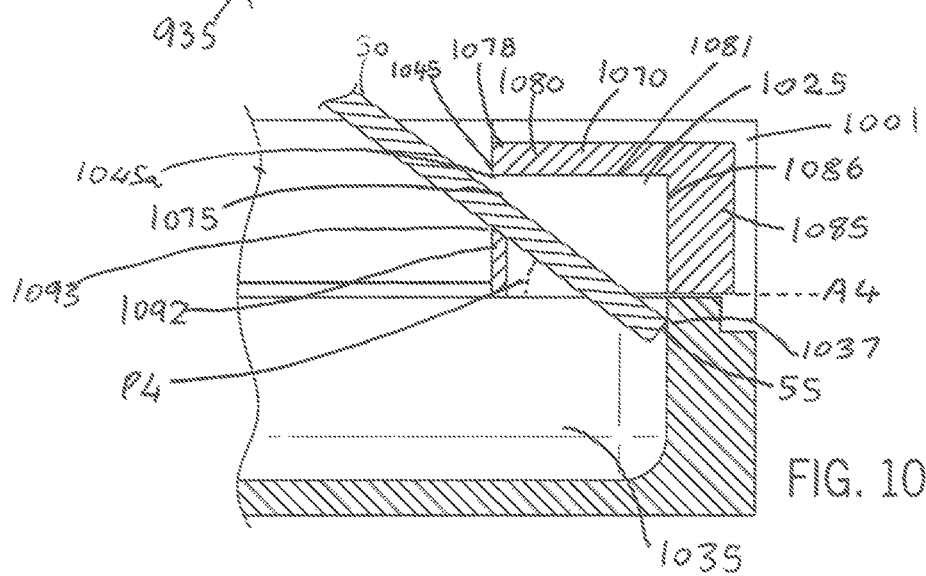
FIG. 10 shows a cross-sectional view of a holder portion in accordance with other embodiments of the invention.

FIG. 10 shows a cross-sectional view of an incense support 1070 in accordance with some further embodiments of the invention. The incense support 1070 is shown with a partial portion of an incense stick 50 positioned in the incense support 1070. In some embodiments, the incense stick 50 can be inserted into the incense support 1070 through an aperture 1075 formed in the incense support 1070 between one or more internal walls or surfaces of the incense support 1070. In some embodiments, the aperture 1075 can comprise a generally round cross-sectional profile. In other embodiments, the cross-sectional profile can be oval or ellipsoidal. In other embodiments, at least a portion of the cross-sectional profile of the aperture 1075 can include a square or rectangular profile. Other embodiments include an aperture 1075 with straight and round edge sections. Based at least on part on this internal structure of the incense support 1070 including the aperture 1075, the incense stick 50 can be positioned at various angles with respect to incense support 1070 as part of an incense burner (e.g., such as incense burner 100). In some embodiments, the aperture 1075 can be formed by at least a portion of an upper section 1080 and a lower section 1092 that includes walls and surfaces that at least partially bound the aperture 1075 and an internal cavity 1025 that is fluidly coupled to ash tray 1035.

In some embodiments, the aperture 1075 can form an entry to internal cavity 1025 created by a combination of these walls or surfaces of the upper section 1080 and lower section 1092. For example, in some embodiments, the incense support 1070 can comprise an upper section 1080 inwardly extending from the first end 1001 coupled to an end section 1085 at the first end 1001. The end section 1085 can be positioned extending generally perpendicular from the upper section 1080, and generally parallel to the lower section 1092. In some embodiments, the upper section 1080 and end section 1085 at least partially surround the internal cavity 1025. In some embodiments, the internal cavity 1025 can comprise a top side 1081 of the upper section 1080, and an end side 1086 of the end section 1085 that extends generally perpendicular from the top side 1081. In some embodiments, the lower section 1092 can form another side of the internal cavity opposite the end side 1086. In some embodiments, at a second end 1078 of the upper section 1080, a wall 1045 can extend towards the internal cavity 1025 generally perpendicular to the end side 1086. In some embodiments, the wall 1045 can extend towards the lower section 1092, and can couple with the top side 1081 with a separation from an aperture wall 1093 of the lower section 1092 that forms the aperture 1075.

In the non-limiting embodiment of FIG. 10, the wall 1045 is shown extending with an end 1045a that can comprise a generally rounded and/or flat surface coupled to the top side 1081. As shown in the non-limiting embodiment of FIG. 10, an incense stick 50 can be positioned through the aperture 1075 supported by the aperture wall 1093 and not to the end 1045a leaving a gap between the outer surface of the incense stick 50 and the wall 1045. One of ordinary skill in the art will recognize that in embodiments where the incense stick 50 includes an outer diameter that is substantially the same or similar as the distance between any portion of the aperture wall 1093 and end 1045a, where the end 1045a is coupled with the incense stick 50, the position and stability behavior of the incense stick 50 will be similar to or the same as described above with respect to the embodiment shown in FIG. 9. In some embodiments, the incense stick 50 can be positioned as shown with a region 52 generally positioned in the internal cavity 1025, and the end 55 extending into the ash tray 1035 and coupling with the cavity wall 1037. In other embodiments, the incense stick 50 can be positioned through the aperture 1075 supported by the aperture wall 1093, with a region 52 generally positioned in the internal cavity 1025, and the end 55 extending into the ash tray 1035 and/or the internal cavity 1025 while not coupling with either the end side 1086 and/or the cavity wall 1037.

In some embodiments of the invention as shown, the incense stick 50 can positioned on the aperture wall 1093 that is angled about the same as the angle P4 from plane A4 (comprising the interface between the internal cavity 1025 and the ash tray 1035), and therefore the angle of the incense stick 50 with respect to the plane A4 is about the same as angle P4. One of ordinary skill in the art can appreciate that the angle P4 can vary based on numerous factors, including, but not limited to, the diameter of the incense stick 50, the extent to which the incense stick 50 extends into the internal cavity 1025, the diameter of the aperture 1075, and the length of the wall 1045 and/or end 1045a geometry, and the shape or angle of the aperture wall 1093 with respect to the plane A4 (similar to that discussed above with respect to the variation of the wall 893 with respect to the plane A2).

In some embodiments, the incense stick 50 can remain in a generally stable position following insertion into the aperture 1075 as the mass of the incense stick 50 can exert a force against the aperture wall 1093. Moreover, friction between the outer surface of the incense stick 50 (either at the end 55 or another portion of the outer surface of the incense stick 50 such as a region coupled to the aperture wall) can maintain the incense stick 50 in a generally stable position. In some embodiments, the position or stability of the position of the incense stick 50 can vary, based on the length and/or mass of the incense stick 50. In some embodiments, once a previously inserted incense stick 50 is reduced in length and/or mass (e.g., due to burning), the incense stick 50 can begin to move within the aperture 1075 and/or internal cavity 1025, and/or cavity wall 1037. For instance, where friction between the outer surface of the incense stick 50 and walls 1093, 1037, and/or friction between the outer surface of the incense stick 50 and the aperture 1075 (e.g., between the incense stick 50 and the aperture wall 1093) can maintain the incense stick 50 in a stable position, the position of the incense stick 50 can begin to become unstable as the length and mass of the incense stick 50 is reduced during burning. For example, in some embodiments, due to gravity, the lower mass of the incense stick 50 can exert a reduced force against any of the walls 1045, 1037, 1093, which can result in movement of the incense stick 50. In some further embodiments, depending on the diameter or resulting burnt length and/or composition of the incense stick 50, the outer surface of the incense stick 50 can also decouple with any of the walls 1045, 1037, 1093. In some embodiments, the length and mass of the incense stick 50 can be reduced (due to burning) to a point where the stability of the position of the remaining portion of the incense stick 50 is no longer stable, the incense stick 50 can decouple from any of the walls 1045, 1037, 1093, and fall into the internal cavity 1025 and the ash tray 1035.

FIG. 11 is a top-front perspective view of another incense burner 1100 embodiment, and FIG. 12 is a perspective view of the incense burner 1100 in accordance with some embodiments of the invention. Further views are shown in FIGS. 15-18, and detailed further below. Referring initially to FIGS. 11 and 12, showing perspective views of an incense burner 1100 in accordance with some embodiments of the invention, in some embodiments, the incense burner 1100 can include a structure that provides an observer with a view of a supported incense stick (e.g., such as an incense stick 50 as previously shown and described). The open architecture of the incense burner 1100 embodiment shown in FIGS. 11 and 12, can enable a user to view an incense material (e.g., such as an incense stick 50) in the incense burner 1100 during the combustion, and potentially view any visible release of volatile combustion products and/or smoke. For example, in some embodiments, the incense burner 1100 can hold the incense stick 50 in an upper portion 1140, allowing combustion to proceed, while enabling volatile combustion products and/or smoke to be released into the air. In some embodiments, the incense burner 1100 can include a base 1110 on which at least a portion of the upper portion 1140 is supported. In some embodiments, the incense burner 1100 includes the upper portion 1140 at least partially coupled to the base 1110. In some embodiments, the base 1110 and upper portion 1140 can be coupled substantially seamlessly, where the transition from the base 1110 to the upper portion 1140 is almost not visible or not visible to the user (not shown). In some embodiments, the base 1110 and upper portion 1140 can be coupled to provide a visible or partially visible gap or seam 1107. Further, some embodiments comprise a first end 1101 that includes an incense support 1170, and an incense stick 50 that can be inserted into the incense support 1170 through an aperture 1175. In some embodiments, the aperture 1175 can be formed or positioned in any of the housings or portions of the incense burner 1100 described herein. As shown, the incense stick 50 can extend at least a partial length of the incense burner 1100 towards the second end 1102 of the incense burner 1100. In some embodiments, the upper portion 1140 can comprise a trough, cavity, or aperture extending at least a partial length of the upper portion 1140. For example, in some embodiments, the upper portion 1140 can comprise a cavity 1145.

The architecture of the incense burner 1100 can enable an incense stick 50 to burn efficiently by suspending the burning end or portion of the incense stick 50 in open space while allowing optimal capture of ash and other solid waste products from the incense stick 50. Further, one or more internal surfaces or structures of the incense support 1170 can enable the incense stick 50 to be positioned mostly or completely within the cavity 1145 so that any burning portion of the incense stick 50 is containing generally within the cavity 1145, and does not extend out of the incense burner 1100. In some embodiments, the cavity 1145 can extend from the first end 1101 extending away from the incense support 1170 towards the second end 1102. In some embodiments, the cavity 1145 can comprise a closed end 1104 as shown. In other embodiments, cavity 1145 can be generally open when the closed end 1104 is absent or is reduced in size or shape. In some embodiments, the incense stick 50 can extend up to, adjacent to, or proximate the closed end 1104 of the second end 1102 of the incense burner 1100. In other embodiments, the cavity 1145 can comprise an open end (not shown) that can enable an incense stick 50 to extend beyond the second end 1102 (i.e., extending outside of the cavity 1145).

Referring to FIG. 13, showing a close-up cutaway perspective view of an end of the incense burner 1100 of FIGS. 11-12 in accordance with some embodiments of the invention, and FIG. 14, showing the exploded assembly view of the incense burner 1100 of FIGS. 11-12 including incense sticks, in some embodiments, the cavity 1145 can comprise two opposite opposed coupled sides 1150*a*, 1150*b* inwardly extending to opposite edges of an ash aperture 1160 that is positioned in the upper portion 1140. When mounted as shown, the incense stick 50 can extend at least a partial length of the ash aperture 1160 towards the second end 1102 of the incense burner 1100, and can be generally aligned with and parallel with the ash aperture 1160. Further, as shown in FIG. 13, in some embodiments, the sides 1150*a*, 1150*b* can extend to a wall 1147 at the first end 1101. In some embodiments, the wall 1147 can extend from the sides 1150*a*, 1150*b* at the first end 1101 adjacent to or coupled to the incense support 1170, and where the aperture 1175 of the incense support 1170 can be positioned though a portion of the wall 1147.

In some embodiments, the incense burner 1100 can include or comprise an ash collection region fluidly coupled to the ash aperture 1160. In some other embodiments, a separate ash collection portion can be mounted to a separate base structure. During use, while any portion of an incense stick 50 undergoing combustion, any ash product formed during combustion can fall under gravity from the incense stick 50 and travel into the ash collection region. In some embodiments, any ash arriving in the ash collection region can be out of sight of a user. In some embodiments, the ash collection region of the incense burner 1100 can be configured to be readily separable from other portions of the incense burner 1100 to enable emptying and disposal of any collected ash product. For example, in some embodiments, the ash aperture 1160 can be positioned so that products of combustion (e.g., such as ash or embers from the incense stick 50) can be received, collected, and/or stored for later disposal. For example, in some embodiments, material from the incense stick 50 can fall through any portion of the ash aperture 1160 into the base 1110. Referring to FIG. 14, in some embodiments, the base 1110 can include an inner perimeter wall 1137 extending around the perimeter of an ash tray 1135 of the base 1110. In some embodiments, the upper portion 1140 can be positioned on the base 1110 proximate to or coupled to a ledge 1142 that extends around the outer perimeter of the base 1110 proximate an inner perimeter wall 1137 that extends at least partially around the ash tray 1135. When positioned as described (and also shown in FIGS. 11-12), the base 1110 of the incense burner 1100 can function a collector of ash or other combustion products, or burnt or virgin portions of the incense stick 50 travel through the ash aperture 1160 and into the ash tray 1135.

In some further embodiments, the incense burner 1100 can include additional cavities for collection of ash, or for storage of accessories including spare incense sticks. For example, in some embodiments, the base 1110 can include an opening 1190 to a storage cavity 1200 that can be used to store additional incense sticks or other incense-related accessories. In some embodiments, the storage cavity 1200 can extend from the first end 1101 at least partially to the second end 1102. Further, in some embodiments, the storage cavity 1200 can be separated from the ash tray 1135 by wall 1205 that extends coupled to the inner perimeter wall 1137 from the first end 1101 at least partially to the second end 1102. In some embodiments, a plurality of incense sticks 60 (shown in FIG. 14) can be positioned in the storage cavity 1200 where any one of the incense sticks 60 can be used as incense stick 50.

Figure 15:
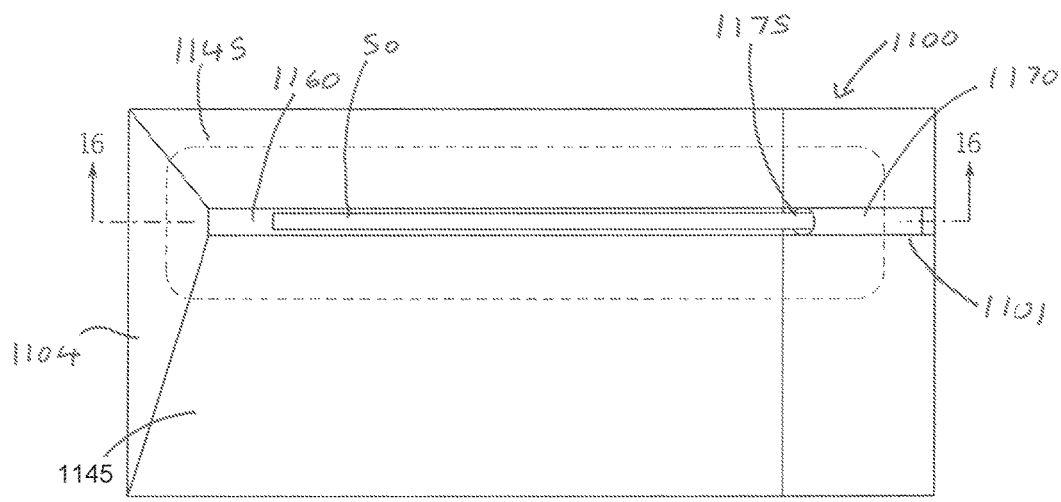
FIG. 15 is a top view of the incense burner of FIGS. 11-12 in accordance with some embodiments of the invention.
Figure 16:
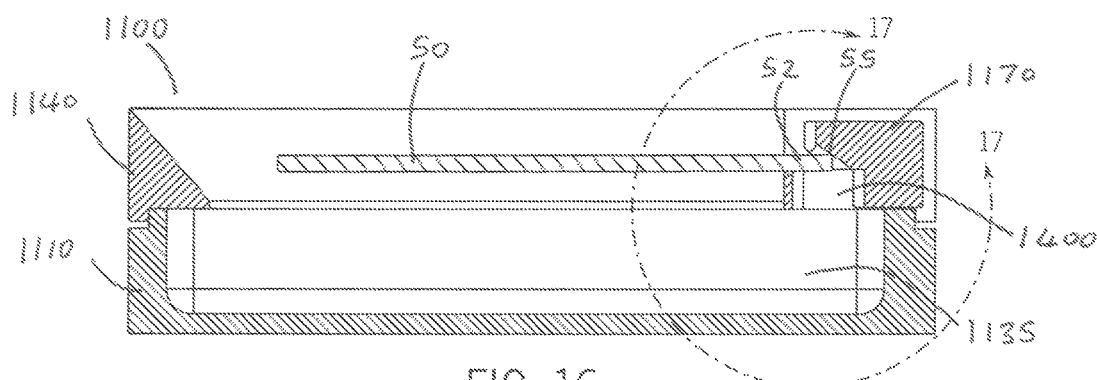
FIG. 16 is a cross-sectional view taken through the cross-section line shown in FIG. 15 in accordance with some embodiments of the invention.

The internal structures responsible for maintaining the position of the incense stick 50 are detailed in FIGS. 15-16, and FIGS. 17-18. For example; FIG. 15 is a top view of the incense burner 1100 of FIGS. 11-12 in accordance with some embodiments of the invention, and FIG. 16 is a cross-sectional view taken through the cross-section line shown in FIG. 15 in accordance with some embodiments of the invention. As discussed earlier, the incense stick 50 can be inserted into the incense support 1170 through an aperture 1175, and based at least on part on the internal structure of the aperture 1175, the incense stick 50 can be positioned at various angles with respect to the incense burner 1100. For example, in some embodiments, the aperture 1175 can be formed through the first end 1101 of the incense burner 1100 and bounded by an upper portion 1410 and a lower portion 1460 that includes walls 1430, 1465, 1470 that at least partially bound the aperture 1175, and a coupled internal cavity 1400 that is coupled to the ash tray 1135. In some embodiments, the aperture 1175 can form an entry to cavity 1145 created by a combination of walls or surfaces of the upper portion 1410 and lower portion 1460. In some embodiments, the aperture 1175 can form a portion of a channel 2000 that can extend from the aperture 1175 towards the coupled internal cavity 1400 to an interface (marked as dotted line plane B). Further, in some embodiments, the channel 2000 can be fluidly coupled to a section or region of the incense burner for collecting ash and other debris (e.g., the ash tray 1135). For example, in some embodiments, the aperture 1175 can be bounded by an upper wall 1450 extending from the aperture 1175 opening adjacent the wall 1147 of the cavity 1145 to a coupled internal cavity 1400. In some embodiments, the coupled internal cavity 1400 can be formed between wall 1425 extending from the upper portion 1410 towards the ash tray 1135, and wall 1465 of the lower portion 1460 that extends from the lower wall 1470 to the ash tray 1135. In some embodiments, the aperture 1175 can comprise a generally round cross-sectional profile. In other embodiments, the cross-sectional profile can be oval or ellipsoidal. In other embodiments, at least a portion of the cross-sectional profile of the aperture 1175 can include a square or rectangular profile. Other embodiments include an aperture 1175 with straight and round edge sections.

Figure 17:
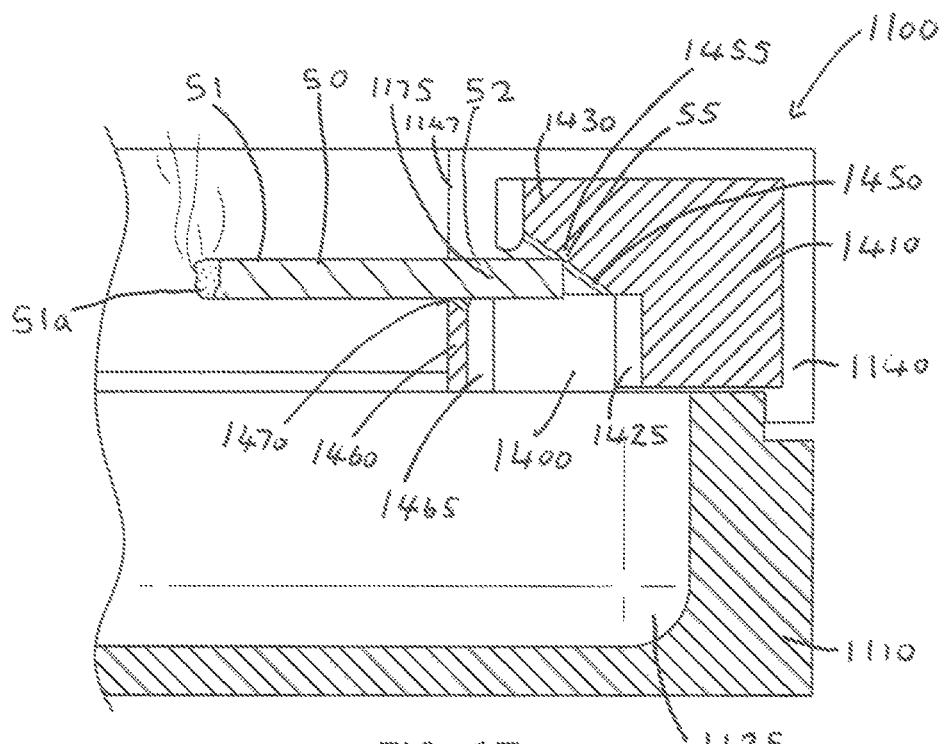
FIG. 17 is a close-up view of a holder portion of the incense burner defined in the FIG. 16 showing a partial portion of an incense stick positioned in the holder portion of the incense burner in accordance with some embodiments of the invention.

In some embodiments of the invention, the channel 2000 can be sloped or angled from the coupled internal cavity 1400. For example, in some embodiments, the angle P5, taken from plane B can be about 30°. In some other embodiments, the angle P5, taken from plane B can be more or less than about 30° in some embodiments. For example, in some embodiments, the angle P5 can be between about 0° and 15°. In some other embodiments, the angle P5 can be between about 15° and 30°. In some further embodiments, the angle P5 can be greater than about 30°. For example, in some embodiments, the angle P5 can be between about 30° and about 45°. In some other embodiments, the angle P5 can be between about 45° and about 60°. In some further embodiments of the invention, the angle P5 can be between about 60° and 80°. In further embodiments, the angle P5 can be greater than about 80° but less than about 90°. Referring to FIG. 17, in some embodiments, a first end 55 of the incense stick 50 can be inserted through the aperture 1175, and the user can slide the incense stick 50 into the channel 2000 until at least a portion of the first end 55 couples with upper wall 1450 at a contact region 1455. In light of the above-mentioned angle P5 and variations of angle P5 with respect to plane B, one of ordinary skill in the art can recognize that the contact region 1455 can change position on the upper wall 1450 based on a number of variables including, but not limited to, the angle P5, the extent to which the incense stick 50 is inserted into the channel 2000, the geometry of the first end 55, or a combination thereof.

In some embodiments, the mass of the incense stick 50 can exert a force against the upper wall 1450 in the contact region 1455 and the lower wall 1470 at the interface with the region 1455. Further, due to friction between the outer surface of the incense stick 50 (either at the end 55 or another portion of the outer surface of the incense stick 50 such as a region 52 adjacent to the end 55) and the contact region 1455 of the upper wall 1450 and/or friction between the outer surface of the incense stick 50 and the lower wall 1470 at the interface with the wall 1147, the incense stick 50 in a remain in a generally stable position following insertion through the aperture 1175. In some further embodiments, the incense stick 50 can remain in a generally stable position following insertion into the channel 2000 where a user has partially inserted the incense stick 50. In this instance, friction between the outer surface of the incense stick 50 in a region 52 coupled to the lower wall 1470 at the interface with the wall 1147 can maintain the incense stick 50 in a generally stable position. In some embodiments, the position or stability of the position of the incense stick 50 can vary based on the length and/or mass of the incense stick 50. In some embodiments, once a previously inserted incense stick 50 is reduced in length and/or mass due to burning), the incense stick 50 can begin to move within the aperture 1175 and channel 2000. For instance, where a combination of friction between the outer surface of the incense stick 50 and a surface of the lower wall 1470, and friction contact between the outer surface of the incense stick 50 and friction contact between the first end 55 and the contact region 1455 maintains the incense stick 50 in a stable position, the position of the incense stick 50 can become unstable as the length and mass of the incense stick 50 is reduced due to reduction following burning. For example, in some embodiments, due to gravity, the lower mass of the incense stick 50 can exert a reduced force against the upper wall 1450 at the end 55, and/or any, surface of the lower wall 1470 (e.g., at the interface with the wall 1147) resulting in movement of the incense stick 50. In some embodiments, depending on the diameter or resulting burnt length and/or composition of the incense stick 50, the outer surface of the incense stick 50 can also decouple from the contact region 1455 of the upper wall 1450.

Figure 18:
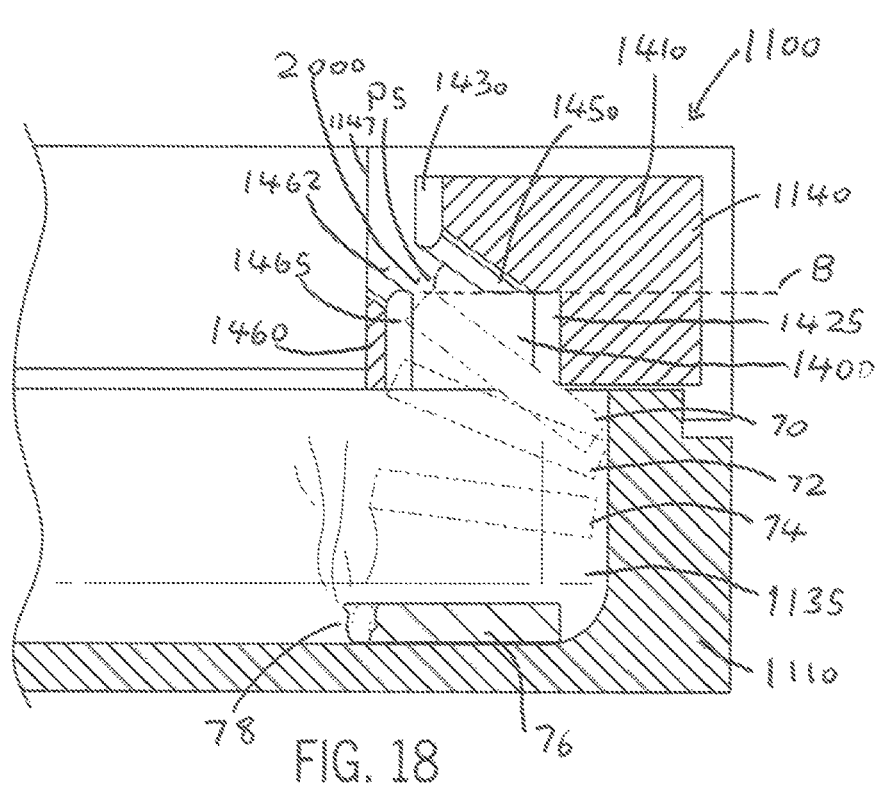
FIG. 18 shows a close-up view of a holder portion of the incense burner defined in the FIG. 16 showing transport of a partial portion of an incense stick previously positioned in the holder portion of the incense burner in accordance with some embodiments of the invention.

In some further embodiments, the position of the incense stick 50 can become unstable following insertion into the channel 2000 where a user has partially inserted the incense stick 50 so the friction between the outer surface of the incense stick 50 (e.g., region 52) and the surface of the lower wall 1462 and/or friction contact between the outer surface of the incense stick 50 and the end 55 at the upper wall 1450 ordinarily maintains the incense stick 50 in a stable position when the incense stick 50 is longer and/or has greater mass. In this instance, as the incense stick 50 burns and its length and mass decrease, friction between a portion of the incense stick 50 and the surface of the lower wall 1462 at the interface with the wall 1147 and/or friction contact between the incense stick 50 at the end 55 and the upper wall 1450 may lessen or no longer be present, thereby causing instability and/or movement of the incense stick 50. In some embodiments, the length and mass of the incense stick 50 can be reduced (due to burning) to a point where the stability of the position of the remaining portion of the incense stick 50 is no longer stable. In this instance, the remaining portion of the incense stick 50 can decouple from the upper wall 1450, and slide over the surface of the lower wall 1462, and travel into the channel 2000. This type of event can be understood by reviewing FIGS. 17 and 18. FIG. 17 is a close-up of an end of the incense burner 1100 showing a partial portion of an incense stick 50 positioned in the holder portion of the incense burner in accordance with some embodiments of the invention, and FIG. 18 is a close-up view of a holder portion of the incense burner 1100 showing a representation of a remaining portion of an incense stick 76 with burning end 78 falling from the coupled internal cavity 1400 to ash tray 1135 (with dotted outlines 70, 72, 74 showing the motion of the incense stick 76 through the incense burner 1100.)

FIG. 19 is a top-front perspective view of another incense burner embodiment, and FIG. 20 is a perspective view of the incense burner in accordance with some embodiments of the invention. Further views are shown in FIGS. 21-24, and detailed further below. Referring initially to FIGS. 19 and 20, showing perspective views of an incense burner 1900 in accordance with some embodiments of the invention, in some embodiments, the incense burner 1900 can include a structure that provides an observer with a view of a supported incense stick (e.g., such as an incense stick 50 as previously shown and described). The open architecture of the incense burner 1900 embodiment shown in FIGS. 19 and 20, can enable a user to view an incense stick (e.g., an incense stick 50) in the incense burner 1900 during the combustion, and potentially view any visible release of volatile combustion products and/or smoke. For example, in some embodiments, the incense burner 1900 can hold an incense stick in an upper portion 1940, allowing combustion to proceed, while enabling volatile combustion products and/or smoke to be released into the air. In some embodiments, the incense burner 1900 can include a base 1910 on which at least a portion of the upper portion 1940 can be supported. In some embodiments, the incense burner 1900 includes the upper portion 1940 at least partially coupled to the base 1910. In some further embodiments, the incense burner 1900 can include a center portion 1920 positioned coupled between the base 1910 and the upper portion 1940 as shown. In some embodiments, the base 1910 and center portion 1920 can be coupled substantially seamlessly where the transition from the base 1910 to the center portion 1920 is almost not visible or not visible to the user (not shown). In some further embodiments, the base 1910 and center portion 1920 can be coupled to provide a visible or partially visible gap or seam 1908. Further, in some embodiments, the center portion 1920 and upper portion 1940 can be coupled substantially seamlessly where the transition from the center portion 1920 to the upper portion 1940 is almost not visible or not visible to the user (not shown). In some embodiments, the center portion 1920 and upper portion 1940 can be coupled to provide a visible or partially visible gap or seam 1907.

Some embodiments of the invention comprise a first end 1901 that includes an incense support 1970, and an incense stick 50 that can be inserted into the incense support 1970 through an aperture 1975. In some embodiments, the aperture 1975 can be formed or positioned in any of the housings or portions of the incense burner 1900 described herein. As shown, the incense stick 50 can extend at least a partial length of the incense burner 1900 towards the second end 1902 of the incense burner 1900. In some embodiments, the upper portion 1940 can comprise a trough, cavity, or aperture extending at least a partial length of the upper portion 1940. For example, in some embodiments, the upper portion 1940 can comprise a cavity 1945. The architecture of the incense burner 1900 can enable an incense stick 50 to burn efficiently by suspending the burning end or portion of the incense stick 50 in open space while allowing optimal capture of ash and other solid waste products from the incense stick 50. In some embodiments of the invention, one or more internal surfaces or structures of the incense support 1970 can enable the incense stick 50 to be positioned mostly or completely within the cavity 1945 so that any burning portion of the incense stick 50 is containing generally within the cavity 1945, and does not extend out of the incense burner 1900 which may cause a safety hazard. For example, in some embodiments, the cavity 1945 can extend from the first end 1901 extending away from the incense support 1970 towards the second end 1902. In some embodiments, the cavity 1945 can comprise a closed end 1904 as shown. In other embodiments, cavity 1945 can be generally open when the closed end 1904 is absent or is reduced in size or shape. In some embodiments, the incense stick 50 can extend up to, adjacent to, or proximate the closed end 1904 of the second end 1902 of the incense burner 1900. In other embodiments, the cavity 1945 can comprise an open end (not shown) that can enable an incense stick 50 to extend beyond the second end 1902 (i.e., extending outside of the cavity 1945).

Figure 21:
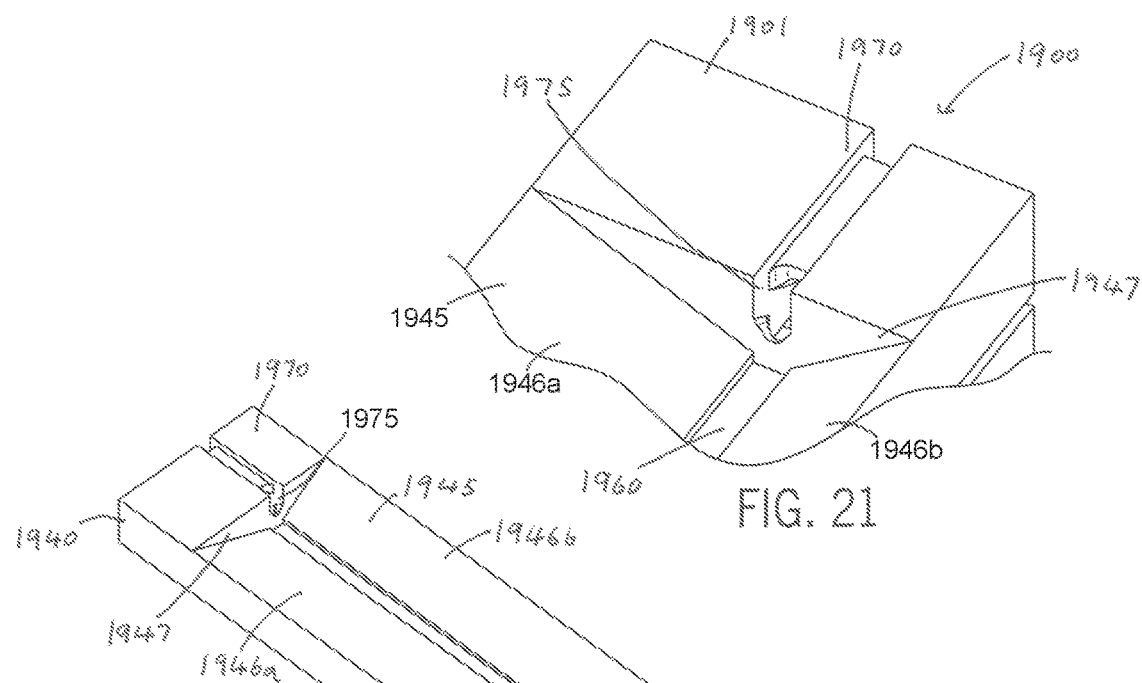
FIG. 21 is a close-up cutaway perspective view of an end of the incense burner of FIGS. 19-20 in accordance with some embodiments of the invention.
Figure 22:
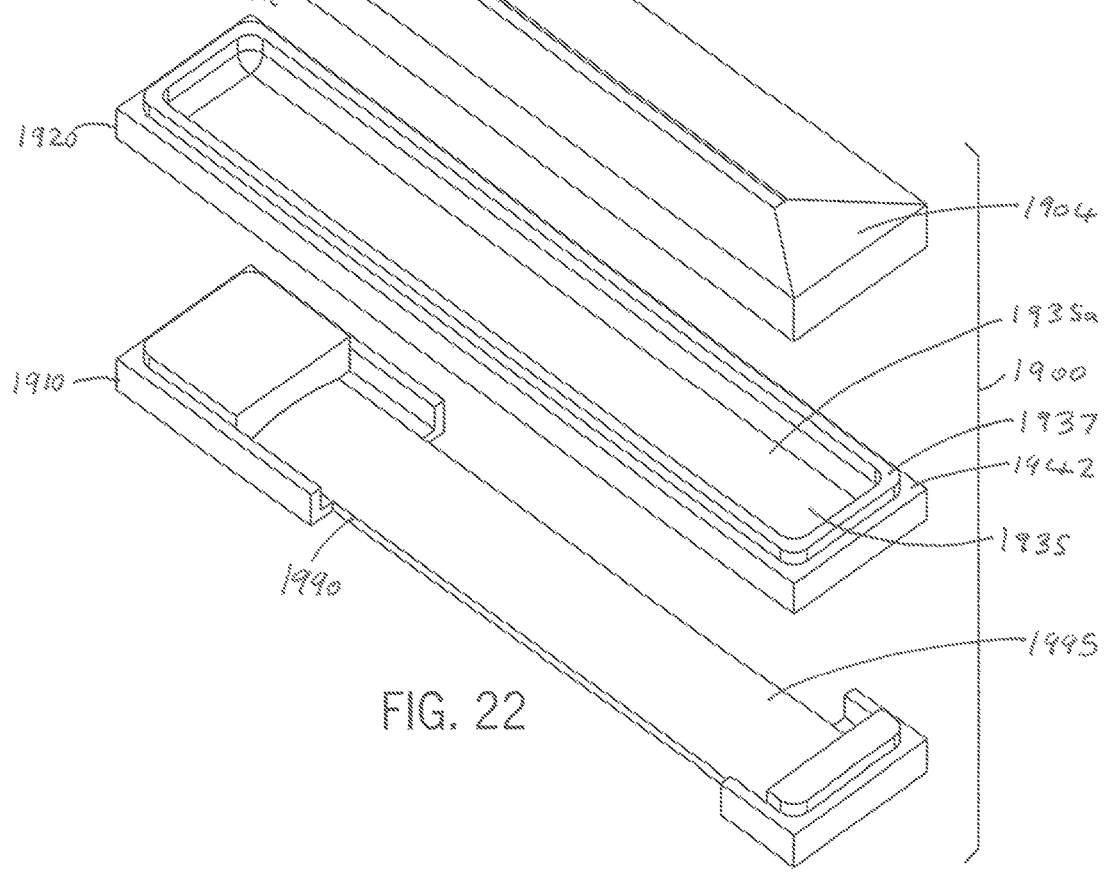
FIG. 22 is an exploded assembly view of the incense burner of FIGS. 19-20 in accordance with some embodiments of the invention.

Referring to FIG. 21, showing a close-up cutaway perspective view of an end of the incense burner 1900 of FIGS. 19-20 in accordance with some embodiments of the invention, and FIG. 22, showing the exploded assembly view of the incense burner 1900 of FIGS. 19-20 including incense sticks, in some embodiments, the cavity 1945 can comprise two opposite opposed coupled sides 1946a, 1946b inwardly extending to opposite edges of an ash aperture 1960 that is positioned in the upper portion 1940. In some embodiments, when mounted as shown, the incense stick 50 can extend at least a partial length of the ash aperture 1960 towards the second end 1902 of the incense burner 1900, and can be generally aligned with and parallel with the ash aperture 1960. In some embodiments, the ash aperture 1960 is positioned substantially centrally in the upper portion 1940 and the sides 1946a 1946b can be substantially the same width. In other embodiments, the ash aperture 1960 can be positioned substantially centrally in the upper portion 1940 and the sides 1946a 1946b can be of unequal width. Further, as shown in FIG. 21, in some embodiments, the sides 1946a, 1946b can extend to a wall 1947 at the first end 1901. In some embodiments, the wall 1947 can extend from the sides 1946a, 1946b at the first end 1901 adjacent to or coupled to the incense support 1970, and where the aperture 1975 of the incense support 1970 can be positioned though a portion of the wall 1947.

In some embodiments, the incense burner 1900 can include or comprise an ash collection region fluidly coupled to the ash aperture 1960. In some other embodiments, a separate ash collection portion can be mounted to a separate base structure. During use, while any portion of an incense stick 50 undergoing combustion, any ash product formed during combustion can fall under gravity from the incense stick 50 and travel into the ash collection region. In some embodiments, any ash arriving in the ash collection region can be out of sight of a user. In some embodiments, the ash collection region of the incense burner 1900 can be configured to be readily separable from other portions of the incense burner 1900 to enable emptying and disposal of any collected ash product. For example, in some embodiments, the ash aperture 1960 can be positioned so that products of combustion (e.g., such as ash or embers from the incense stick 50) can be received, collected, and/or stored for later disposal. For example, in some embodiments, material from the incense stick 50 can fall through any portion of the ash aperture 1960 into the center portion 1920. Referring to FIG. 22, in some embodiments, the center portion 1920 can include an inner perimeter wall 1937 extending around the perimeter of an ash tray 1935 of the center portion 1920. In some embodiments, the upper portion 1940 can be positioned on the center portion 1920 proximate to or coupled to a ledge 1942 that extends around the outer perimeter of the center portion 1920 proximate an inner perimeter wall 1937 that extends at least partially around the ash tray 1935. When positioned as described (and also shown in FIGS. 19-20), the center portion 1920 of the incense burner 1900 can function a collector of ash or other combustion products, or burnt or virgin portions of the incense stick 50 travel through the ash aperture 1960 and into the ash tray 1935.

In some further embodiments, the incense burner 1900 can include additional cavities for collection of ash, or for storage of accessories including spare incense sticks. For example, in some embodiments, the base 1910 can include an opening 1990 to a storage cavity 1995 that can be used to store additional incense sticks or other incense-related accessories. In some embodiments, the storage cavity 1995 can extend from the first end 1901 at least partially to the second end 1902. In the non-limiting embodiments shown, the storage cavity 1995 of the center portion 1920 can be separated from the ash tray 1935 by bottom wall 1935a of the center portion 1920, and thus ash or other debris is prevented from entering the storage cavity 1995 in the adjacently coupled base 1910. In some embodiments, a plurality of incense sticks (not shown) can be positioned in the storage cavity 1995. The internal structures responsible for maintaining the position of an inserted incense stick are shown in FIG. 24. As discussed in relation to previously described embodiments, the incense stick 50 can be inserted into the incense support 1970 through an aperture 1975, and based at least on part on the internal structure of the aperture 1975 that includes the internal cavity 1974, and channel 1979 extending from the aperture 1975 to the internal cavity 1974, the incense stick 50 can be positioned at various angles with respect to the incense burner 1900. The structure, use, and operation of the incense support 1970 is similar or the same as that described earlier with respect to the incense burner 1100, and specifically as described and shown in FIGS. 17 and 18, and the internal geometry of the incense support 1970 is the same or similar to incense support 1170, and the scale and relative lengths may be the same or different.

Figure 27:
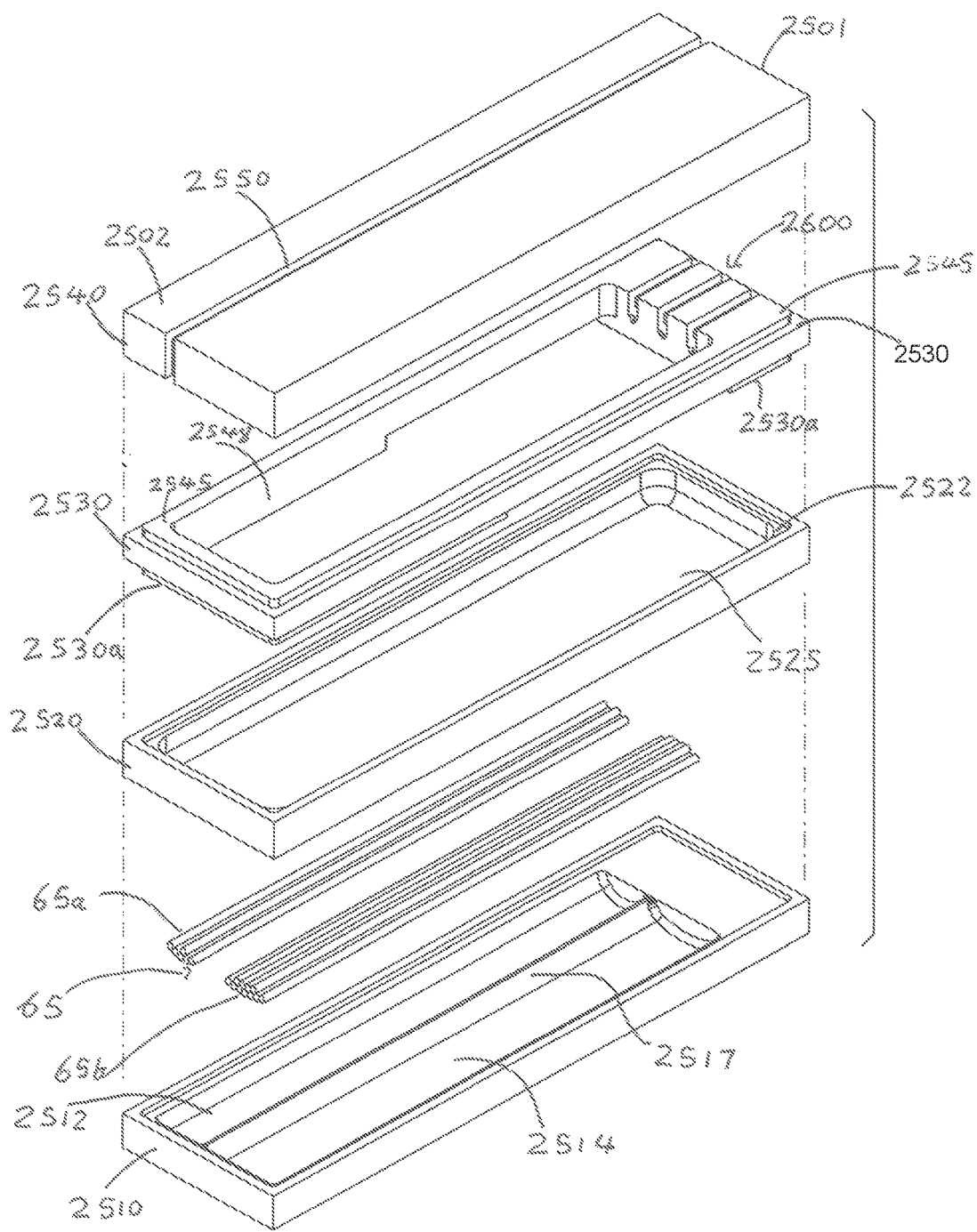
FIG. 27 is an exploded assembly view of the incense burner of FIG. 25 in accordance with some embodiments of the invention.
Figure 28:
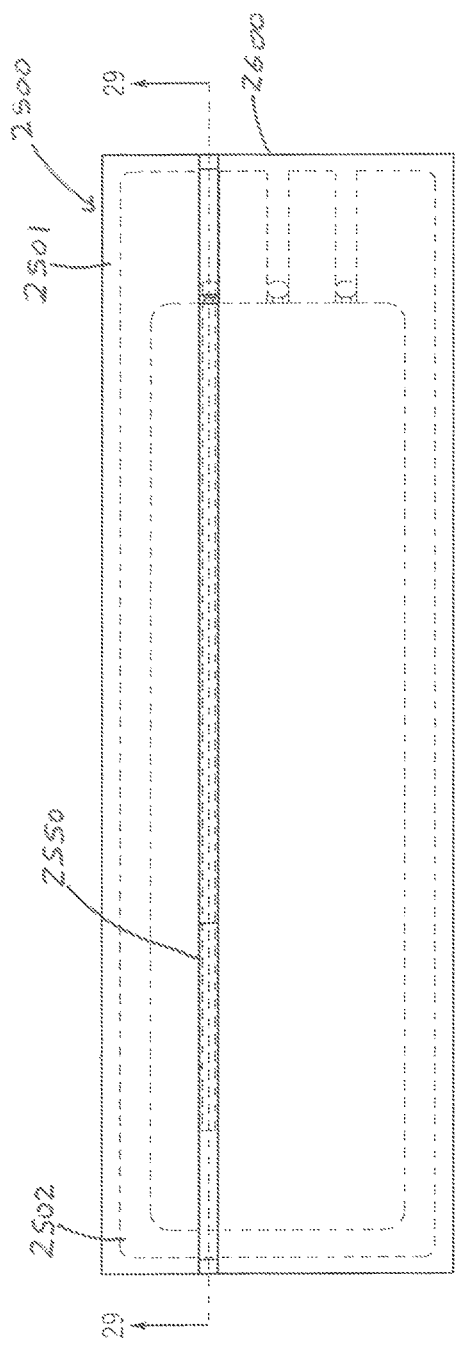
FIG. 28 is top view of an incense burner including inner regions shown in dotted lines in accordance with some embodiments of the invention.
Figure 29:
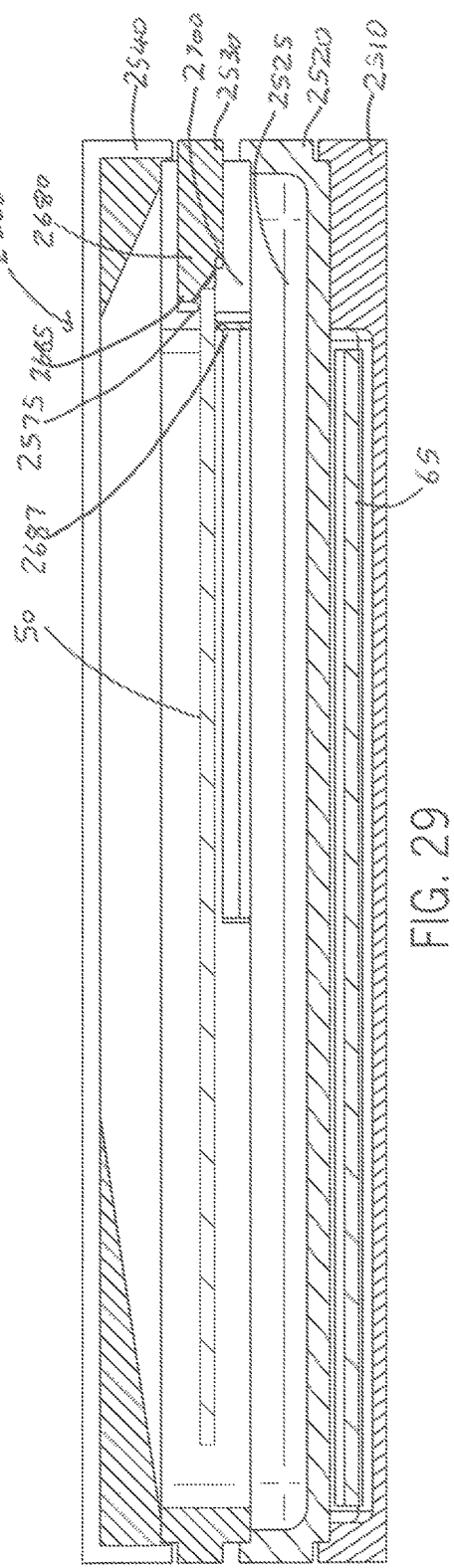
FIG. 29 is a cross-sectional view taken through the cross-section line shown in FIG. 28 in accordance with some embodiments of the invention.

Some embodiments of the invention include an incense burner that can include a structure that at least partially encloses the incense material undergoing combustion. In some embodiments, the incense burner can include a structure (e.g., a lid or cover) that can at least partially prevent or obscure the viewing of the incense material undergoing combustion. In some embodiments, the incense burner can hold the incense material in a region of the incense burner that is at least partially enclosed, allowing combustion to proceed, while enabling volatile combustion products and/or smoke to be released into the air in and around the apparatus. Accordingly, due to the at least partially closed architecture, a user can be prevented from viewing at least a portion of the incense material in the incense burner during the combustion. For example, referring to FIGS. 25-29, some embodiments include an incense burner 2500 that includes an optional lid portion 2540. In some embodiments, the incense burner 2500 can include a structure for channeling or guiding volatile combustion products and/or smoke from the incense burner (e.g., such as passage or chimney) enabling release or escape of volatile combustion products from the combustion process. In some circumstances, a user can view any visible release of volatile combustion products and/or smoke as it is produced by one or more burning incense materials inside the incense burner 2500. In some embodiments, the structure can be coupled to one or more outlets 2550 that can enable the outflow of the volatile combustion products and/or smoke within the incense burner 2500. In some embodiments, the one or more outlets 2550 can comprise one or more holes or vents, and/or one or more channels. In some embodiments, the one or more outlets 2550 can be proximate or immediately adjacent to the incense material undergoing combustion. In some further embodiments, the one or more outlets 2550 can be positioned away from the incense material undergoing combustion and the volatile combustion products and/or smoke can be guided or channeled to one or more outlets 2550 as described above. Further details of the incense burner 2500 are provided in FIGS. 26-29. For example, FIG. 26 is a perspective view of the incense burner of FIG. 25 with the lid portion 2540 removed in accordance with some embodiments of the invention. Further, FIG. 27 is an exploded assembly view of the incense burner 2500 of FIG. 25, and FIG. 28 is top view of an incense burner 2500 including inner regions shown in dotted lines in accordance with some embodiments of the invention. Further, FIG. 29 is a cross-sectional view taken through the cross-section line shown in FIG. 28 in accordance with some embodiments of the invention.

In some embodiments, a portion of the incense burner 2500 can include a structure that can be arranged coupled to a base 2510 (or can form the base 2510) that can be arranged so that spare, and/or unused, and/or partially used incense materials can be received, collected, and/or stored. For example, some embodiments include a storage compartment or section 2512. In some embodiments, the incense burner 2500 can include a base 2510 that includes the storage compartment or section 2512. Some embodiments include a single storage compartment or section (e.g., section 2512), and other embodiments include a plurality of storage compartment or sections (e.g., the additional compartment or section 2514 coupled to the compartment or section 2512 and separated by a wall 2517). In some embodiments, the storage compartment or sections 2512, 2514 can be configured to be readily separable from other portions of the incense burner to enable re-stocking with incense materials, emptying, cleaning. In some embodiments, the storage compartment or section can be positioned coupled below an ash tray 2520, and the ash tray 2520 can be positioned coupled below an upper portion 2530 coupled to the lid portion 2540 described above. In some embodiments, a plurality of incense sticks 65 can be positioned in compartment or sections 2512, 2514. For example, some embodiments include incense sticks 65a positioned in storage compartment or sections 2512, and/or incense sticks 65b positioned in storage compartment or sections 2514.

In some embodiments, the base 2510 and ash tray 2520 can be coupled substantially seamlessly where the transition from the base 2510 to the ash tray 2520 is almost not visible or not visible to the user (not shown). In some embodiments, the base 2510 and ash tray 2520 can be coupled to provide a visible or partially visible gap or seam 2532. Further, in some embodiments, the ash tray 2520 and upper portion 2530 can be coupled substantially seamlessly where the transition from the ash tray 2520 to the upper portion 2530 is almost not visible or not visible to the user (not shown). In some embodiments, the ash tray 2520 and upper portion 2530 can be coupled to provide a visible or partially visible gap or seam 2532. In some embodiments, the ash tray 2520 can include a ledge 2522 extending around at least a portion of the ash tray into which an extension 2530a (e.g., a guide) on the upper portion 2530 can couple. Further, in some embodiments, the lid portion 2540 and the upper portion 2530 can be coupled substantially seamlessly where the transition from the lid portion 2540 to the upper portion 2530 is almost not visible or not visible to the user (not shown). In some embodiments, the lid portion 2540 and upper portion 2530 can be coupled to provide a visible or partially visible gap or seam 2532.

Some embodiments of the invention comprise a first end 2501 that includes incense supports 2600 that can comprise a plurality of apertures for insertion of an incense material (e.g., such as incense stick 50). For example, some embodiments include a first incense support 2625 comprising an aperture 2630, and/or a second incense support 2650 comprising an aperture 2655, and/or a third incense support 2675 comprising an aperture 2680. In some embodiments, any one or more of the apertures 2630, 2655, 2680 can be formed or positioned in any of the housings or portions of the incense burner 2500 described herein. In some embodiments, the incense supports 2600 can be distributed substantially equally spaced at the first end 2501 as shown. In other embodiments, the incense supports 2600 can be distributed substantially unequally spaced (not shown). As shown in FIG. 29, at least one of the incense supports 2600 can comprise an inserted incense stick 50 that can extend at least a partial length of the incense burner 2500 towards the second end 2502 of the incense burner 2500. One of ordinary skill in the art will recognize that any of the incense supports 2600 can include an inserted incense stick 50. For example, some embodiments include two incense sticks 50 with each incense stick positioned into an aperture selected from aperture 2630, 2655, 2680, and in other embodiments, all three apertures 2630, 2655, 2680 can include an incense stick 50.

In some embodiments, the upper portion 2530 can comprise a trough, cavity, or aperture extending at least a partial length of the upper portion 2530. For example, in some embodiments, the upper portion 2530 can comprise a cavity 2548. The architecture of the incense burner 2500 can enable an incense stick 50 to burn efficiently by suspending the burning end or portion of the incense stick 50 in open space while allowing optimal capture of ash and other solid waste products from the incense stick 50. Further, in some embodiments, one or more internal surfaces or structures of the incense supports 2600 can enable up to three incense stick 50 to be positioned mostly or completely within the cavity 2548 so that any burning portion of any one of the three incense stick 50 is containing generally within the cavity 2548, and does not extend out of the incense burner 2500 which may cause a safety hazard. For example, in some embodiments, the cavity 2548 can extend from the first end 2501 extending away from the incense support 1970 towards the second end 2502. In some embodiments, following burning of any incense stick 50 in any of the incense supports 2600, ash or other products of combustion and/or partially burnt portions of incense sticks 50 can fall from any of the incense supports 2600 and into the ash tray 2520. In some embodiments, any ash arriving in the ash tray 2520 can be out of sight of a user. In some embodiments, the ash tray 2520 of the incense burner 2500 can be configured to be readily separable from other portions of the incense burner 2500 to enable emptying and disposal of any collected ash product. For example, in some embodiments, the ash tray 2520 can be positioned so that products of combustion (e.g., such as ash or embers from the incense sticks 50) can be received, collected, and/or stored for later disposal. For example, in some embodiments, material from the incense stick 50 can fall from any of the incense supports 2600 and into the ash tray 2520. In this non-limiting embodiment, the storage compartment or sections 2512, 2514 of base 2510 are separated from the ash tray 2520 by bottom wall 2525 of the ash tray 2520, and thus ash or other debris is prevented from entering the storage compartment or sections 2512, 2514.

The internal structures responsible for maintaining the position of an inserted incense stick are shown in FIG. 29. The structure, use, and operation of the incense supports 2600 are similar or the same as that described earlier with respect to the incense burner 1100 and incense burner 1900, and the internal geometry of the incense supports 2600 is the same or similar to incense supports 1170, 1970, and the scale and relative lengths may be the same or different. For example, the incense stick 50 can be inserted into any of the incense supports 2600 (e.g., through any one or more of the apertures 2630, 2655, 2680), and based at least on part on the internal structure of the apertures 2630, 2655, 2680 that includes the internal cavity 2700, and channel 2575 (where any of the apertures 2630, 2655, 2680 can include the channel 2575) extending to the internal cavity 2700, the incense stick 50 can be positioned at various angles with respect to the incense burner 2500. In some embodiments, any one or more of the aperture 2630, 2655, 2680 can be bound by an upper wall 2685 extending from the cavity 2548 to the coupled channel 2575 to the wall 2687 similar or the same as the structures defined for incense burner 1100 and incense burner 1900.

Figure 30:
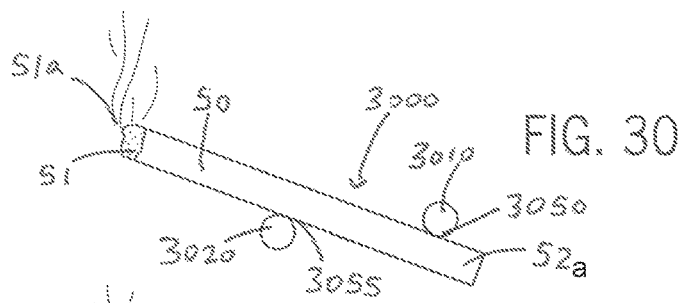
FIGS. 30-38 illustrate incense stick holder architectures in accordance with some embodiments of the invention.

FIGS. 30-38 illustrate incense stick holder architectures in accordance with some embodiments of the invention. As shown an incense stick 50 including a first end 51 with a burning end 51a can extend to a second end 52a that can be positioned coupled to structures that can be used in with or in place of any of the incense supports described earlier with respect to any of the incense burners 100, 1100, 1900, or 2500. For example, FIG. 30 illustrates an incense stick holder architecture 3000 in accordance with some embodiments of the invention. In some embodiments, the stick holder architecture 3000 comprise a lower support 3020 and an upper support 3010, where an incense stick 50 can be placed at least partially between the lower support 3020 and upper support 3010 where the incense stick 50 can be coupled to the lower support 3020 at the contact area 3055 of the incense stick 50, and a contact area 3050 of the incense stick 50 with the upper support 3010. In some embodiments, as the burning end 51a approaches the second end 52a, the mass of the incense stick 50 is reduced, resulting in less force exerted between the lower support 3020 and the contact area 3055, and/or the upper support 3010 and the contact area 3050. In some embodiments, at least a portion of the incense stick 50 can decouple from the lower support 3020 and/or the upper support 3010.

Figure 31:
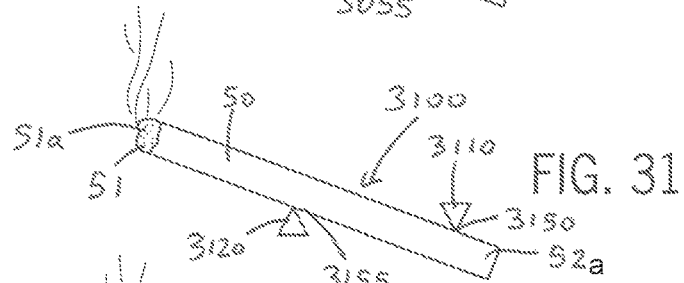

FIG. 31 illustrates an incense stick holder architecture 3100 in accordance with some embodiments of the invention. In some embodiments, the stick holder architecture 3100 comprise a lower support 3120 and an upper support 3110, where an incense stick 50 can be placed at least partially between the lower support 3120 and upper support 3110 where the incense stick 50 can be coupled to the lower support 3120 at the contact area 3155 of the incense stick 50, and a contact area 3150 of the incense stick 50 with the upper support 3110. In some embodiments, as the burning end 51a approaches the second end 52, the mass of the incense stick 50 is reduced, resulting in less force exerted between the lower support 3120 and the contact area 3155, and/or the upper support 3110 and the contact area 3150. In some embodiments, at least a portion of the incense stick 50 can decouple from the lower support 3120 and/or the upper support 3110.

Figure 32:
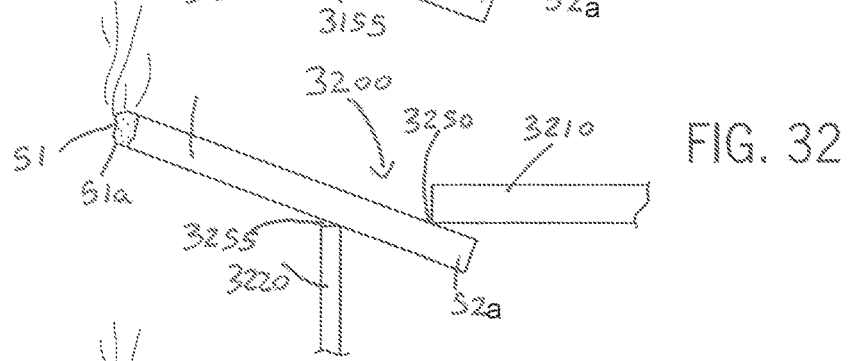

FIG. 32 illustrates an incense stick holder architecture 3200 in accordance with some embodiments of the invention. In some embodiments, the stick holder architecture 3200 comprise a lower support 3220 and an upper support 3210, where an incense stick 50 can be placed at least partially between the lower support 3220 and upper support 3210 where the incense stick 50 can be coupled to the lower support 3220 at the contact area 3255 of the incense stick 50, and a contact area 3250 of the incense stick 50 with the upper support 3210. In some embodiments, as the burning end 51a approaches the second end 52a, the mass of the incense stick 50 is reduced, resulting in less force exerted between the lower support 3220 and the contact area 3255, and/or the upper support 3210 and the contact area 3250, In some embodiments, at least a portion of the incense stick 50 can decouple from the lower support 3220 and/or the upper support 3210.

Figure 33:
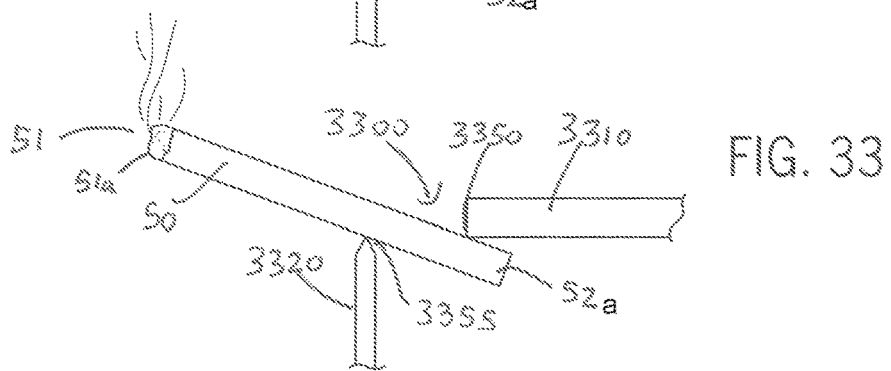

FIG. 33 illustrates an incense stick holder architecture 3300 in accordance with some embodiments of the invention. In some embodiments, the stick holder architecture 3300 comprise a lower support 3320 and an upper support 3310, where an incense stick 50 can be placed at least partially between the lower support 3320 and upper support 3310 where the incense stick 50 can be coupled to the lower support 3320 at the contact area 3355 of the incense stick 50, and a contact area 3350 of the incense stick 50 with the upper support 3310. In some embodiments, as the burning end 51a approaches the second end 52a, the mass of the incense stick 50 is reduced, resulting in less force exerted between the lower support 3320 and the contact area 3355, and/or the upper support 3310 and the contact area 3350. In some embodiments, at least a portion of the incense stick 50 can decouple from the lower support 3320 and/or the upper support 3310.

Figure 34:
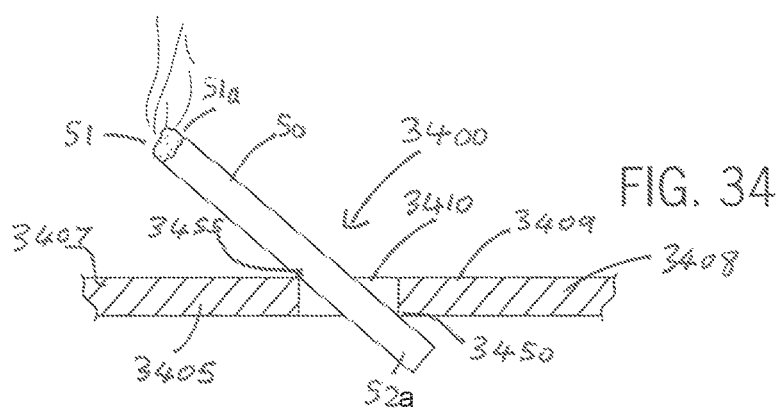

FIG. 34 illustrates an incense stick holder architecture 3400 in accordance with some embodiments of the invention. Some embodiments include a support side 3407 at a first end 3405 with a through aperture 3410 between first end 3405 and a second end 3409 including support side 3408. In some embodiments, an incense stick 50 can be placed at least partially through aperture 3410 where the incense stick 50 can be coupled to the support side 3407 at the contact area 3455 of the incense stick 50, and a contact area 3450 of the incense stick 50 with the support side 3408. In some embodiments, as the burning end Ma approaches the second end 52a, the mass of the incense stick 50 is reduced, resulting in less force exerted between the contact areas 3450 and/or 3455 in some embodiments, at least a portion of the incense stick 50 can decouple from either or both of the contact areas 3450, 3455.

Figure 35:
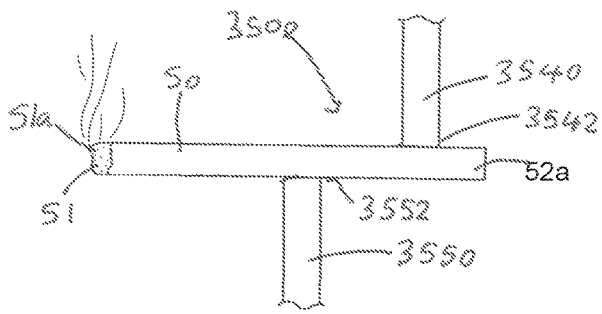

FIG. 35 illustrates an incense stick holder architecture 3500 in accordance with some embodiments of the invention. In some embodiments, the stick holder architecture 3500 comprise a lower support 3550 and an upper support 3540, where an incense stick 50 can be placed at least partially between the lower support 3550 and upper support 3540 where the incense stick 50 can be coupled to the lower support 3550 at the contact area 3552 of the incense stick 50, and a contact area 3542 of the incense stick 50 with the upper support 3540. In some embodiments, as the burning end 51a approaches the second end 52a, the mass of the incense stick 50 is reduced, resulting in less force exerted between the lower support 3550 and the contact area 3552, and/or the upper support 3540 and the contact area 3542. In some embodiments, at least a portion of the incense stick 50 can decouple from the lower support 3550 and/or the upper support 3540.

Figure 36:
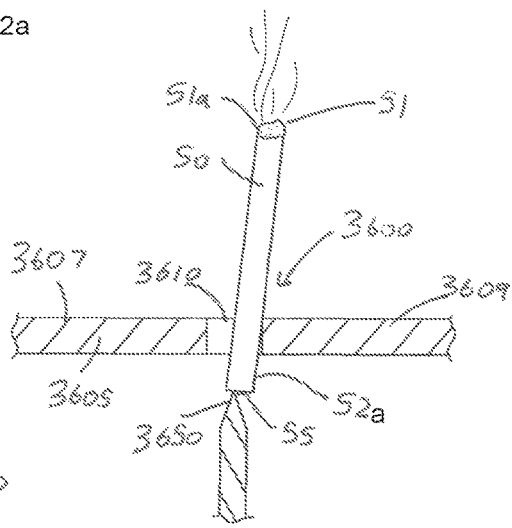

FIG. 36 illustrates an incense stick holder architecture 3600 in accordance with some embodiments of the invention. Some embodiments include a lower support 3650, and a support 3605 with a through aperture 3610 between first end 3607 and second end 3609 at either side of the through aperture 3610. In some embodiments, as the burning end 51a approaches the second end 52a, the mass of the incense stick 50 is reduced, resulting in less force exerted between the end 55 of the incense stick 50 and the lower support 3650, and/or between the incense stick 50 and sides of the aperture 3610. In some embodiments, at least a portion of the incense stick 50 can decouple from lower support 3650, and/or between the incense stick 50 and sides of the aperture 3610.

Figure 37:
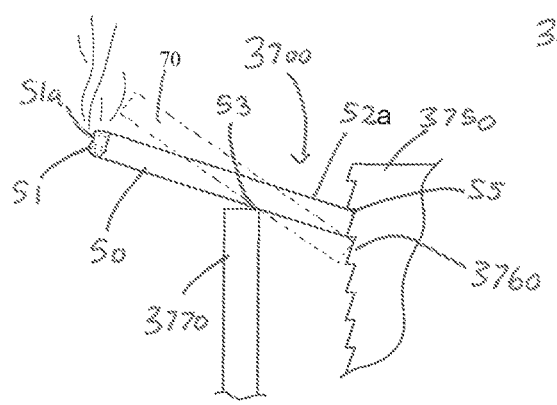

FIG. 37 illustrates an incense stick holder architecture 3700 in accordance with some embodiments of the invention. Some embodiments include lower support 3770, and a surface support comprising surface structure 3760 of wall 3750. In some embodiments, as the burning end 51a approaches the second end 52a, the mass of the incense stick 50 is reduced, resulting in less force exerted between the region 53 of the stick 50 and the lower support 3770, and/or between the end 55 of the incense stick 50 and surface structure 3760 of wall 3750. In some embodiments, at least a portion of the incense stick 50 can decouple from in the region 53 of the incense stick 50 and the lower support 3770, and/or between the end 55 of the incense stick 50 and surface structure 3760 of wall 3750

Figure 38:
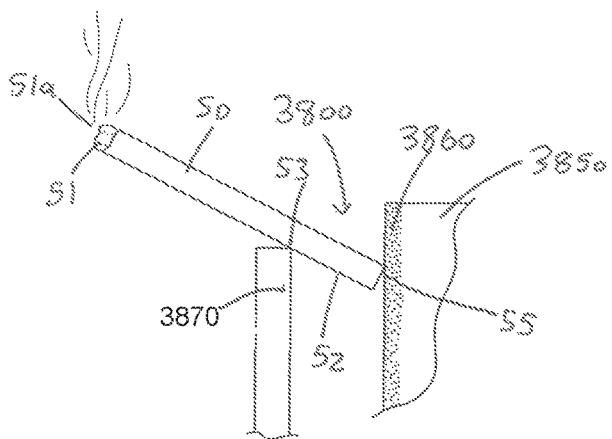

FIG. 38 illustrates an incense stick holder architecture 3800 in accordance with some embodiments of the invention. Some embodiments include lower support 3870, and a surface support comprising surface structure 3860 of wall 3850. In some embodiments, as the burning end 51a approaches the second end 52a, the mass of the incense stick 50 is reduced, resulting in less force exerted between the region 53 of the incense stick 50 and the lower support 3870, and/or between the end 55 of the incense stick 50 and surface structure 3860 of wall 3850. In some embodiments, at least a portion of the incense stick 50 can decouple from in the region 53 of the incense stick 50 and the lower support 3870, and/or between the end 55 of the incense stick 50 and surface structure 3860 of wall 3850.

Some embodiments include positioning or centering structures to aid in support, positioning, or balance of an inserted incense stick into any aperture of the incense burners 100, 1100, 1900, or 2500. For example, FIG. 39 is an elevation view of an incense stick orifice structure 3900 in accordance with some embodiments of the invention. FIG. 40 is a section view of the incense stick orifice structure 3900 of FIG. 39 in accordance with some embodiments of the invention. In some embodiments, this incense stick orifice structure 3900 can be used in with or an place of any of the incense supports described earlier with respect to any of the incense burners 100, 1100, 1900, or 2500. Incense stick 90 is shown in outline in FIG. 40 showing positioning of the incense stick 90 in the aperture 3910 that comprises a generally square or rectangular cross-section with coupled faces 3915

Further, FIG. 41 is an elevation view of an incense stick orifice structure 4100 in accordance with some embodiments of the invention, and FIG. 42 is a section view of the incense stick orifice structure 4100 of FIG. 41 in accordance with some embodiments of the invention. In some embodiments, this incense stick orifice structure 4100 can be used in with or an place of any of the incense supports described earlier with respect to any of the incense burners 100, 1100, 1900, or 2500. Incense stick 90 is shown in outline in FIG. 42 showing positioning of the incense stick 95 in the aperture 4110 that comprises a generally rounded cross-section with curved face 4115

Further, FIG. 43 is an elevation view of an incense stick orifice structure 4300 in accordance with some embodiments of the invention, and FIG. 44 is a section view of the incense stick orifice structure 4300 of FIG. 43 in accordance with some embodiments of the invention. In some embodiments, this incense stick orifice structure 4300 can be used in with or an place of any of the incense supports described earlier with respect to any of the incense burners 100, 1100, 1900, or 2500. Incense stick 98 is shown with positioning of the incense stick 98 in the space 4310 formed between any one or combination of surfaces 4305.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims

The invention claimed is:

1. An incense holder assembly comprising:
at least an upper housing with at least one orifice positioned through a top surface of the upper housing, the at least one orifice fluidly coupled to at least one internal chamber of the incense holder assembly, the at least one orifice configured and arranged with the at least one internal chamber as a cantilever support when coupled with at least one inserted incense material comprising a first predetermined length sufficient to maintain a certain cantilever load on at least a portion of the at least one orifice or at least one inner surface of the at least one internal chamber, the certain cantilever load being a cantilever load sufficient to maintain the at least one inserted incense material in a stable position; and
wherein following a reduction of the first predetermined length by burning to a second predetermining length resulting in production of ash, the at least one inserted incense material exerting an insufficient cantilever load on at least a portion of the at least one orifice and at least one inner surface of the at least one internal chamber, the at least one inserted incense material drops out of the at least one orifice and into the at least one internal chamber; and
wherein the at least one internal chamber is fluidly coupled to at least one ash aperture or conduit that extends at least a partial longitudinal length of the upper housing, the at least one ash aperture or conduit configured and arranged to enable the ash to pass through the upper housing and into the at least one internal chamber.

2. An incense holder assembly comprising:
at least one base including at least one cavity;
at least one ash collector coupled to the at least one base;
an upper housing comprising a first end including at least one incense material support the at least one incense material support including at least one incense aperture configured and arranged to support an incense structure inserted at least partially into the at least one incense aperture;
at least one external cavity positioned coupled to the at least one incense material support, the at least one external cavity fluidly coupled to the at least one ash collector;
at least one channel fluidly extending from the at least one incense aperture to at least one internal cavity;
at least two incense material support surfaces configured and arranged to at least partially support the incense structure by coupling to at least one side of the incense structure, and wherein at least one of the at least two incense material support surfaces is positioned within at least one of the at least one channel and the at least one internal cavity, and wherein at least one of the at least two incense material support surfaces is adjacent to or proximate the at least one aperture; and
at least one ash aperture extending at least a partial longitudinal length of the upper housing and the at least one external cavity, and fluidly coupled through the upper housing to the at least one ash collector, the at least one ash aperture configured and arranged to enable ash to pass through the at least one external cavity and upper housing and into the at least one internal chamber.

3. The incense holder assembly of claim 2, wherein the at least two incense material support surfaces are configured and arranged to provide support to the incense structure based at least in part on gravity-induced force on at least one of the at least two incense material support sides exerted by the incense structure.

4. The incense holder assembly of claim 2, wherein the upper housing includes the at least one external cavity.

5. The incense holder assembly of claim 2, wherein the at least one external cavity comprises at least two oppositely opposed sides extending from opposite sides of the at least one ash aperture.

6. The incense holder assembly of claim 5, wherein the at least one ash aperture is positioned substantially centrally in the upper housing extending from adjacent the at least one incense aperture at the first end at least partially to an opposite end of the upper housing.

7. The incense holder assembly of claim 5, wherein the at least one ash aperture is positioned off-center in the upper housing extending from adjacent the at least one incense aperture at the first end at least partially to an opposite end of the upper housing.

8. The incense holder assembly of claim 2, wherein the at least one channel comprises the at least two incense material support surfaces.

9. The incense holder assembly of claim 8, wherein the at least one channel is configured and arranged to support an inserted incense stick extending at least partially, from the first end of the upper housing towards an opposite end of the upper housing.

10. The incense holder assembly of claim 2, further comprising at least one storage cavity.

11. The incense holder assembly of claim 10, wherein the at least one storage cavity is positioned in the at least one base layer and positioned at least partially beneath and separated from the at least one ash collector.

12. The incense holder assembly of claim 2, further comprising a lid coupled to the upper housing and extending at least partially across the at least one external cavity.

13. The incense holder assembly of claim 12, wherein the lid includes at least one vent fluidly coupled to the at least one external cavity and the at least one incense aperture.

14. The incense holder assembly of claim 2, wherein the at least one incense material support comprises three incense material supports, wherein each incense material support includes an incense aperture.

15. The incense holder assembly of claim 2, wherein the upper housing includes an open second end.

16. The incense holder assembly of claim 2, wherein the upper housing includes a closed second end, and the at least one external cavity comprises a trough.

17. The incense holder assembly of claim 2, where the at least one cavity comprises the at least one ash collector.

18. An incense holder manufacturing method comprising:
providing at least one base including at least one cavity;
providing at least one ash collector in at least one ash collector layer;
providing an upper housing comprising a first end including at least one incense material support configured to be coupled to the at least one base, the at least one incense material support including at least one incense aperture configured and arranged to support an incense structure, and wherein the upper housing includes at least one external cavity positioned coupled to the at least one incense material support, the at least one external cavity fluidly coupled to the at least one ash collector;
providing at least one channel fluidly extending from the at least one incense aperture to at least one internal cavity;
providing or assembling at least two incense material support surfaces configured and arranged to at least partially support the incense structure by coupling to at least one surface of the incense structure, and wherein at least one of the at least two incense material support surfaces is positioned within at least one of the at least one channel and the at least one internal cavity, and wherein at least one of the at least two incense material support surfaces is adjacent to or proximate the at least one aperture; and
providing at least one ash aperture extending at least a partial longitudinal length of the upper housing and the at least one external cavity and fluidly coupled through the upper housing to the at least one ash collector, the at least one ash aperture configured and arranged to enable ash to pass through the at least one external cavity and upper housing and into the at least one internal chamber.

19. The method of claim 18, wherein the at least two incense material support surfaces comprise at least one surface of at least one of the at least one base, the at least one ash collector and the upper housing.

20. The method of claim 18, further comprising providing at least one storage cavity, positioned in the at least one base layer and positioned beneath and separated from the at least one ash collector.

21. The method of claim 18, further comprising providing a lid configured to be coupled to the upper housing and extending at least partially across the at least one external cavity, the lid including at least one vent fluidly coupled to the at least one external cavity, and the at least one incense aperture.

\* \* \* \* \*